(12) United States Patent
Ono et al.

(10) Patent No.: US 8,541,024 B2
(45) Date of Patent: Sep. 24, 2013

(54) FILM-COATED SCORED TABLET

(75) Inventors: Akihiko Ono, Osaka (JP); Naomi Nagaoka, Osaka (JP); Shigeyuki Marunaka, Osaka (JP); Yukihiro Nomura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/063,515

(22) PCT Filed: Sep. 15, 2009

(86) PCT No.: PCT/JP2009/066071
§ 371 (c)(1),
(2), (4) Date: May 26, 2011

(87) PCT Pub. No.: WO2010/032717
PCT Pub. Date: Mar. 25, 2010

(65) Prior Publication Data
US 2011/0244040 A1    Oct. 6, 2011

(30) Foreign Application Priority Data

Sep. 16, 2008 (JP) .................................. 2008-236778

(51) Int. Cl.
*A61K 9/20* (2006.01)

(52) U.S. Cl.
USPC ............................ 424/464; 424/465; 424/468

(58) Field of Classification Search
None
See application file for complete search history.

(56) References Cited

U.S. PATENT DOCUMENTS

| | | | |
|---|---|---|---|
| 5,520,929 A | 5/1996 | Makino et al. | |
| 6,161,260 A * | 12/2000 | Flewitt | D24/101 |
| 6,342,248 B1 * | 1/2002 | Miyabe et al. | 424/467 |
| 2006/0160834 A1 * | 7/2006 | Fong et al. | 514/278 |
| 2006/0228409 A1 * | 10/2006 | Miyabe et al. | 424/464 |
| 2008/0009533 A1 * | 1/2008 | Tino et al. | 514/374 |

FOREIGN PATENT DOCUMENTS

| | | |
|---|---|---|
| JP | 10-137 U | 6/1998 |
| JP | 2007-308488 A | 11/2007 |

OTHER PUBLICATIONS

International Preliminary Report on Patentability issued Apr. 19, 2011, in PCT/JP2009/066071, 7 pages.
Kawabata et al., "Jozai no Keitai to Bunkatsu-Bunkatsu no Shiyasusa to Juryo Hensa," Journal of Practical Pharmacy, 2000, 51(5):1424-1429.

* cited by examiner

*Primary Examiner* — Hasan Ahmed
(74) *Attorney, Agent, or Firm* — Foley & Lardner LLP

(57) ABSTRACT

A film-coated scored tablet in which the forms of respective parts associated with a score line are optimized so as to more preferably divide the film along the score line is provided.

9 Claims, 20 Drawing Sheets

| 1 | UPPER SURFACE | L | DIAMETER OF MAJOR AXIS OF OVAL SHAPE |
| 2 | LOWER SURFACE | S | DIAMETER OF MINOR AXIS OF OVAL SHAPE |
| 3 | PERIPHERAL SIDE SURFACE | d | DEPTH OF V-SHAPED GROOVE |
| 4 | V-SHAPED GROOVE (SCORE LINE) | h | HEIGHT OF ELEVATION OF UPPER SURFACE OR LOWER SURFACE |
| 4 1 | BOTTOM OF V-SHAPED GROOVE | t | TOTAL THICKNESS |
| θ | INNER ANGLE OF V SHAPE OF V-SHAPED GROOVE | | |

(a)

(b)

(a)

(b)

(a)

R10

(b)

R11
R10

(c)

α
S
R10

(a)

(b)

(c)

(a)

(b)

(a)

(b)

FILM-COATED SCORED TABLET

TECHNICAL FIELD

The present invention relates to a film-coated scored tablet in which a score line is formed on a plain tablet and the plain tablet is coated with a film coating.

BACKGROUND OF THE INVENTION

A film-coated tablet, also referred to as a film-coating tablet or a film-coat tablet, is a preparation obtained by coating the surface of a plain tablet (uncoated tablet) obtained by compression filling a powder or the like with a film comprising a water-soluble polymer(s) or the like. The purpose of coating a plain tablet with a film is, for example, to protect the plain tablet from external light, atmosphere (humidity and oxygen) or the like, to mask the taste, smell or the like of the medicinal agent contained in the plain tablet, to enhance the appearance of the tablet and the like.

On the other hand, there is a scored tablet (also referred to as "dividing tablet") provided with a groove called a "score line" on the surface of a plain tablet. The purpose of providing the score line is to enable a tablet to be easily divided by applying a force to the tablet by a human in order to adjust the dose or the like.

As for a general constitution of the scored tablet (an embodiment of the score line), for example, a detailed description is given in Patent Document 1 or the like.

However, as a result of a detailed study about the divisibility of conventional scored tablets conducted by the present inventors, although various embodiments with respect to general scored tablets in which only a score line is provided on a plain tablet have been proposed, they found that there was a problem as described below in the embodiment in which a score line is provided further on a film-coated tablet, and that a sufficient study about the score line from the viewpoint of dividing the film-coated tablet in such a manner that the film coincides with the plain tablet was not made.

The problem found by the present inventors is a problem that the coating film on the surface of the tablet is not divided along the score line as intended.

That is, in the case where a film-coated scored tablet 100 as shown in FIG. 10(*a*) is divided along a score line 200, as shown in FIG. 10(*b*), a plain tablet portion 101 is divided as intended at the bottom of the groove of the score line 200 as the start point. However, a film 102 is not always divided as intended at the bottom of the groove of the score line, and as shown in FIG. 10(*b*), the film is peeled off from the surface of the plain tablet in the vicinity of the bottom of the groove, and finally, it is ripped and divided into two at a position leaned toward either divided piece in the end. Further, as a region denoted by the reference numeral 300 in FIG. 10(*b*), also in a back side portion corresponding to the score line, unintended peeling and ripping of the film occur on the surface of the plain tablet. Even in the case where a score line is provided on the back surface side, the same phenomenon as in the score line of the upper surface shown in FIG. 10(*b*) occurs.

As described above, when such a conventional film-coated scored tablet is divided, around the divided surface of the divided piece, only the film protrudes from the plain tablet or the film is torn and the surface of the plain tablet is exposed. In either case, it is not preferred in terms of appearance.

PRIOR ART DOCUMENTS

Patent Documents

Patent Document 1: JP-A-2007-308488

SUMMARY OF INVENTION

Technical Problems

An object of the invention is to solve the above-mentioned problem and to provide a film-coated scored tablet in which the forms of respective parts associated with a score line are optimized so as to more preferably divide the film along the score line.

Solution to Problems

As a result of intensive studies, the present inventors found that there is a specific combination for achieving the above-mentioned object in the forms associated with a line drawn by the bottom of a V-shaped groove serving as a score line, an inner angle of the V-shaped groove, a depth of the V-shaped groove and a thickness of a plain tablet at the portion, and thus completed the invention.

That is, the invention is directed to the followings or the like.

(1) A film-coated scored tablet comprising a tablet being coated with a film coating on a plain tablet having score lines, wherein the scored tablet has an upper surface and a lower surface whose peripheral shape is an oval shape, and a peripheral side surface, the upper surface and the lower surface are gradually elevated from the peripheral edge toward the center thereof, and a V-shaped groove as the score line is provided on each of the upper surface and the lower surface along the minor axis of the oval shape;

an inner angle of the V shape of the V-shaped groove is from 50° to 90°;

a path of the bottom of the V-shaped groove is elevated more on the center side than on the peripheral edge sides of each of the upper surface and the lower surface;

a ratio of a depth d of the V-shaped groove in the center of each of the upper surface and the lower surface to a height h of the elevation of the surface (d/h) is from 0.4 to 1.0; and a ratio of a value obtained by doubling the depth d of the V-shaped groove (2d) in the center of each of the upper surface and the lower surface to a total thickness t of the scored tablet (2d/t) is from 0.2 to 0.5.

(2) A film-coated scored tablet comprising a tablet being coated with a film coating on a plain tablet having score lines, wherein the scored tablet has an upper surface and a lower surface whose peripheral shape is an oval shape, and a peripheral side surface, the upper surface and the lower surface are gradually elevated from the peripheral edge toward the center thereof, and a V-shaped groove as the score line is provided on each of the upper surface and the lower surface along the minor axis of the oval shape;

an inner angle of the V shape of the V-shaped groove is from 50° to 90';

a path of the bottom of the V-shaped groove is elevated more on the center side than on the peripheral edge sides of each of the upper surface and the lower surface;

a ratio of a depth d of the V-shaped groove in the center of each of the upper surface and the lower surface to a height h of the elevation of the surface (d/h) is from 0.4 to 0.9; and a ratio of a value obtained by doubling the depth d of the V-shaped groove (2d) in the center of each of the upper surface and the lower surface to a total thickness t of the scored tablet (2d/t) is from 0.2 to 0.4.

(3) The film-coated scored tablet according to the above (1), wherein the oval shape is an oval shape which does not have straight-line portions.

(4) The film-coated scored tablet according to the above (1), wherein a ratio of the diameter of the minor axis S to the diameter of the major axis L (S/L) of the oval shape is from 0.4 to 0.6.

(5) The film-coated scored tablet according to the above (1), wherein the diameter of the major axis L of the oval shape is from 8 mm to 12 mm.

(6) The film-coated scored tablet according to the above (1), wherein the inner angle of the V shape of the V-shaped groove is 70°.

(7) The film-coated scored tablet according the above (1), wherein the depth d is from 0.5 to 0.8 mm.

(8) The film-coated scored tablet according to the above (1), wherein a bending strength represented by a force required for dividing the film-coated scored tablet when the force is applied thereto so as to divide the tablet at the score line is 50 N or less.

(9) The film-coated scored tablet according to the above (1), which contains 2-({6-[(3R)-3-aminopiperidin-1-yl]-3-methyl-2,4-dioxo-3,4-dihydropyrimidin-1(2H)-yl}methyl) benzonitrile or a salt thereof.

(10) The film-coated scored tablet according to the above (1), which contains 2-ethoxy-1-[[2'-(5-oxo-2,5-dihydro-1,2,4-oxadiazol-3-yl)biphenyl-4-yl]methyl]-1H-benzimidazole-7-carboxylic acid or a salt thereof.

Advantageous Effect of Invention

The film coated scored tablet (also, referred to as "the scored tablet") has the following constitutions (a) to (e) as major characteristics, and by possessing these characteristics at the same time, the configuration capable of dividing the film coinciding with the main body of the plain tablet along the score line as intended is achieved.

(a) A V-shaped groove as a score line is provided on both upper surface and lower surface (hereinafter sometimes referred to as both surfaces) of the tablet.

First, the V-shaped groove itself is in the form of a groove which is preferred to induce dividing most. The forms and dimensions of the respective parts of the groove are as follows. As described below, they are important to control the division of the film on the surface of the plain tablet.

Further, by providing the score line on both surfaces of the tablet, the start point and the end point of the dividing of the scored tablet are established, and thus, peeling of the film on the back surface in which a score line is not provided as a region 300 shown in FIG. 10(b) is prevented from occurring. A relationship between the score lines on both surfaces and the divisibility of the film will be described later as a synergistic effect with the embodiment of the V-shaped groove.

(b) The inner angle of the V shape of the V-shaped groove is from 50° to 90° (preferably 60° to 80°, more preferably 70°).

Within this angle range, the film is more surely ripped at the bottom-most portion of the V-shaped groove serving as the score line. If the inner angle of the V shape is less than 50°, the dividing is very difficult (difficult to divide), and further, the yield of a coating liquid during film coating process is decreased. On the other hand, if the angle exceeds 100°, although dividing is easy (easy to divide), the uniformity of half tablets after dividing tends to be decreased, and further, unintended peeling and ripping of the film are liable to occur.

(c) The path of the bottom of the V-shaped groove is elevated more on the center side than on the peripheral edge sides.

FIG. 2(a) schematically shows a cross-section when the scored tablet is divided at the score line. In the drawing, the path of the bottom 41 of the V-shaped groove is drawn with the thickest solid line, and the divided surface of the plain tablet is hatched. The path of the bottom 41 of the V-shaped groove on the upper surface side describes an elevated curve APB reaching a peak at the center part P, and the path of the bottom 42 of the V-shaped groove on the lower surface side describes an elevated curve CQD reaching a peak at the center part Q.

Further, FIG. 2(b) schematically shows how the form of the cross section including the bottom of the V-shaped groove changes and is separated into two when the scored tablet is divided.

When the scored tablet is tried to be divided from the upper surface side by applying a force, as shown in FIG. 2(b), first, a stress is concentrated on the center part P which is the peak of the elevation on the upper surface side, and dividing starts at the one point, and thereafter, this portion is separated into P and P' and apart farthest from each other. Due to this, the film also starts to be ripped at one point of the center part P with a high probability. At this time, by setting the inner angle of the V shape of the V-shaped groove as in the above (b), the probability that the film starts to be ripped is increased. Further, in the invention, the dividing of the film with beautiful appearance is achieved by interacting the condition that the path of the bottom of the V-shaped groove is elevated (the above (c)) and the condition that the inner angle of the V shape is set to a specific range (the above (b)) with each other.

The ripping of the film occurring at the center part P proceeds to both end parts A and B along the path of the bottom 41 of the groove as shown in FIG. 2(b) as the scored tablet is being divided. As described above, by allowing the ripping of the film to start at one point of the center and allowing the ripping of the film to proceed along the score line, a phenomenon in which the film is ripped at a position leaned toward either divided piece is prevented. Further, the ripping of the film reaches both end parts C and D of the groove on the lower surface side through the side surface, and proceeds to the peak portion Q of the elevated center along the path of the bottom 42 of the groove. Accordingly, also in the lower surface side, the ripping of the film proceeds along the path of the bottom of the score line with a high probability.

As described above, by preferably determining the shape of the cross-section of the V-shaped groove and elevating the path of the bottom of the V-shaped groove of each of the both surfaces toward the center, the film can be ripped at one point, and further, the ripping can be allowed to proceed sequentially as intended. As a result, divided pieces with beautiful appearance without causing protrusion of the film from the plain tablet can be obtained.

On the other hand, in the case where the path of the bottom of the V-shaped groove of the score line is linear, the dividing of the plain tablet or ripping of the film starts at the same time over the entire length of the score line on both surfaces. In such a ripping manner, it is not clear if the film is ripped along the path of the bottom of the V-shaped groove, and as stated in the description of the prior art, the probability that unintended peeling of the film occurs is increased, and therefore, divided pieces with beautiful appearance cannot be obtained.

(d) A ratio of a depth d of the V-shaped groove in the center of each of the both surfaces of the scored tablet to a height h of the elevation of the surface (d/h) is from 0.4 to 1.0 (preferably, 0.4 to 0.9).

FIG. 4 shows the shape of the cross-section of the scored tablet when the tablet is cut along the major axis perpendicularly to the minor axis. For facilitating the understanding of dimensional relationships among the respective parts, the curvatures of both elevated surfaces, the sizes of the V-shaped grooves and the like are described with exaggeration.

The "depth d of the V-shaped groove in the center of the surface" as used herein is, when explanation is made using the V-shaped groove on the upper surface side as an example, a distance between the center part P of the elevated V-shaped groove in FIG. 4 and a design hypothetical peak part P1 of the elevated upper surface.

The hypothetical peak part P1 of the upper surface is a design point necessary when the scored tablet is designed, and a peak of the elevated curved surface notched by the V-shaped groove. In the case where the hypothetical peak part P1 is determined in a product, a point of intersection between the elevated curved line of the peak portion deduced from the curvatures of both sides of the V-shaped groove and the center axis Y may be determined by drawing a picture.

On the other hand, as shown in FIG. 4, the actual depth of the V-shaped groove of a product is a step height d1 between the center part P of the elevated V-shaped groove and the shoulder part P2 of the opening of the groove. A difference k between the design depth d of the V-shaped groove and the actual step height d1 is from about 0.001 mm to 0.01 mm which is very small value.

Further, the "height h of the elevation of the surface" as used herein is, when explanation is made using FIG. 4, in the case of the upper surface, a height of the hypothetical peak part P1 in the center of the upper surface by taking a design flat surface S1 determined by the peripheral edge of the upper surface to be a reference surface. The same shall apply also to the lower surface, and the "height h of the elevation of the surface" is a height of the hypothetical peak part Q1 in the center of the lower surface by taking a design flat surface S2 to be a reference surface.

In the invention, the reason why the ratio d/h is focused on as an important parameter is that the ratio affects the divisibility (ease of dividing and uniformity of half tablets after dividing) and the inhibitory effect on unintended peeling or ripping of the film after dividing.

By setting the ratio d/h in this range, a favorable divisibility (ease of dividing and uniformity of half tablets after dividing) and inhibitory effect on unintended peeling or ripping of the film after dividing are satisfied. If the ratio d/h is less than 0.4, it is extremely difficult to divide the tablet (difficult to divide), and if the ratio d/h exceeds 1.0, although the divisibility (ease of dividing and uniformity of half tablets after dividing) is favorable, unintended peeling and ripping of the film are liable to occur.

(e) A ratio of a value obtained by doubling the depth d of the V-shaped groove (2d) in the center of each of the both surfaces of the scored tablet to a total thickness t of the scored tablet (2d/t) is from 0.2 to 0.5 (preferably 0.2 to 0.4).

The "total thickness t of the scored tablet" as used herein is a distance between the design hypothetical peak part P1 of the elevated upper surface in the center and the design hypothetical peak part Q1 of the elevated lower surface in the center.

In the invention, the reason why the ratio 2d/t is focused on as an important parameter is that the ratio affects the divisibility (ease of dividing and uniformity of half tablets after dividing).

By setting the ratio 2d/t in this range, a favorable divisibility (ease of dividing and uniformity of half tablets after dividing) is obtained. If the ratio 2d/t is less than 0.2, dividing is extremely difficult (difficult to divide), and if the ratio 2d/t exceeds 0.5, although the dividing is easy (easy to divide), the uniformity of half tablets after dividing tends to be decreased.

BRIEF DESCRIPTION OF THE DRAWINGS

FIG. 10(a) shows a side surface of the scored tablet so as to see the profile of the score line; and FIG. 10(b) is a partially enlarged cross-sectional view schematically showing a state of the score line when the scored tablet is divided.

DETAILED DESCRIPTION OF INVENTION

Hereinafter, the invention will be described with reference to specific embodiments.

The "upper surface" and the "lower surface" as used herein are nominal designations for convenience sake for illustrating one surface and the other surface constituting the scored tablet in an identifiable manner, and do not limit the upper and lower positions of the scored tablet. The description with respect to the upper surface including the score line is applied also to the lower surface as such.

Figure 1:
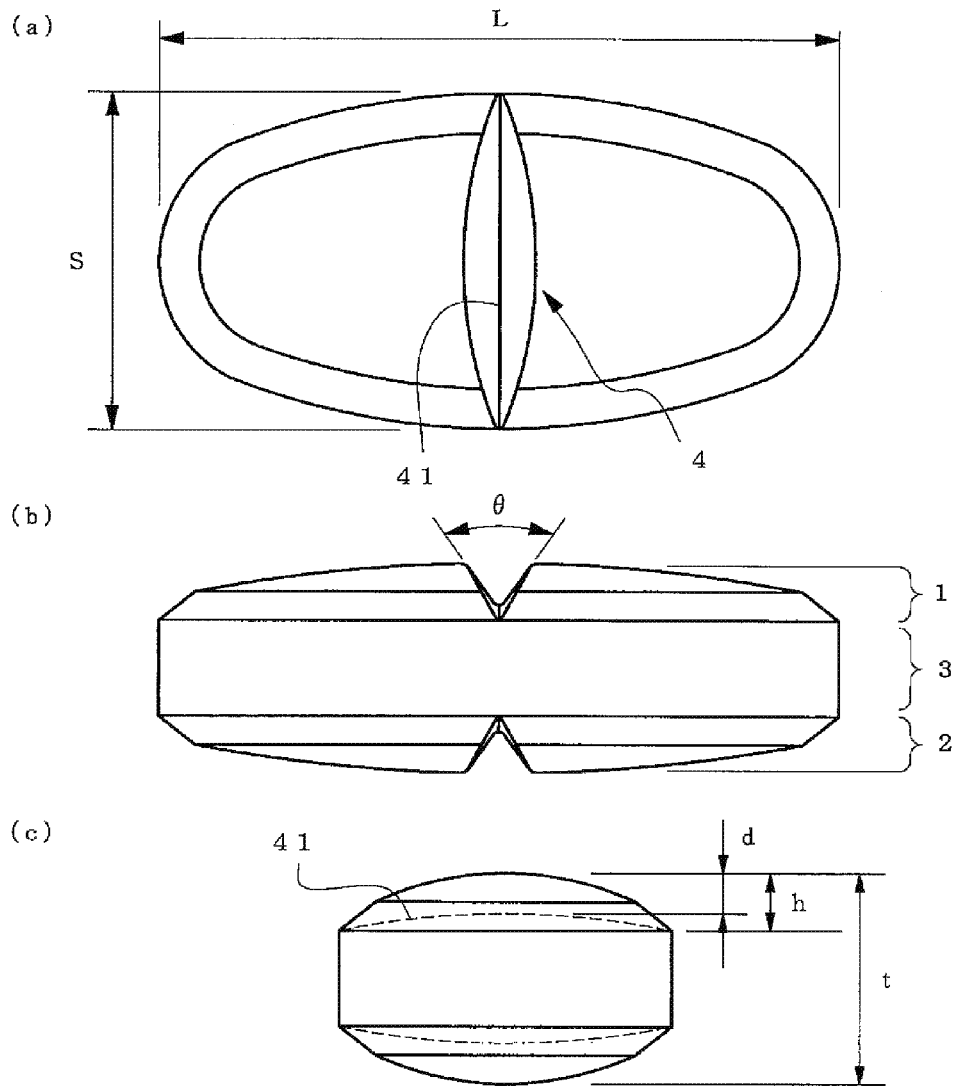
FIG. 1 is a view schematically showing a structure of one example of the scored tablet.

FIG. 1 is a view schematically showing a structure of one example of the scored tablet. The scored tablet comprises a plain tablet having a score line formed thereon and coated with a film coating. The film coating layer is thin, and therefore is not shown in the figure.

As shown in FIGS. 1(a) and (b), the scored tablet has an upper surface 1 and a lower surface 2, each of which peripheral shapes is an oval shape, and a peripheral side surface 3 disposed therebetween. The upper surface 1 and the lower surface 2 are gradually elevated from the peripheral edge toward the center thereof. A V-shaped groove 4 as a score line is provided on each of the upper surface 1 and the lower surface 2 along the minor axis of the oval shape. Here, an inner angle θ of the V shape of the V-shaped groove 4 shown in FIG. 1(b) is from 50° to 90°. Further, as shown in FIG. 1(c), a path of the bottom 41 of the V-shaped groove 4 describes a line such that it is elevated more on the center side than on the peripheral edge sides of each of the upper and lower surfaces.

Further, in the center of each of the both surfaces, a combination of three conditions: the degree of elevation of each of the both surfaces, the thickness of the peripheral side surface and the elevated path of the bottom of the V-shaped groove in the center is selected in such a manner that d/h=0.4 to 1.0 (preferably 0.4 to 0.9), and 2d/t=0.2 to 0.5 (preferably 0.2 to 0.4), and thus, a film-coated scored tablet having a preferred divisibility is achieved.

The peripheral shape of the upper surface and the lower surface of the scored tablet is an oval shape (the score line is formed along the minor axis) from the viewpoint that the divisibility is excellent because the force is easily applied to the score line with a finger or the like.

Figure 3:
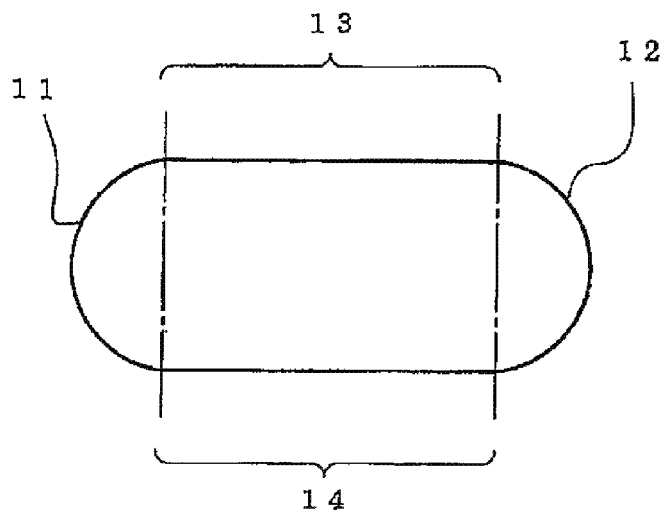
FIG. 3 is a view illustrating variations of an oval shape which is the peripheral shape of each of the upper surface and the lower surface of the scored tablet.
Figure 3:
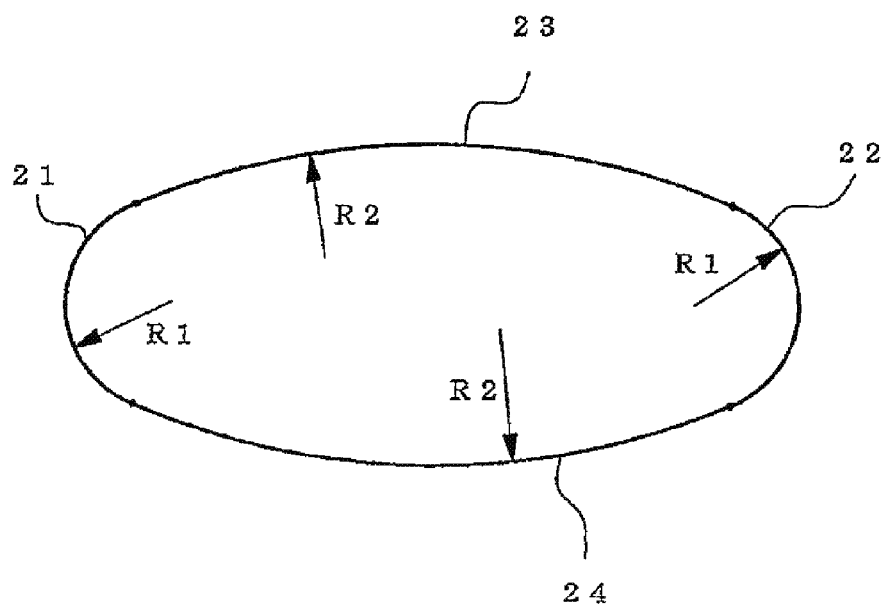

Examples of the oval shape include an oval shape having straight-line portions as shown in FIG. 3(a) (that is, a so-called oblong oval shape comprising two semicircular arc portions 11 and 12, and straight-line portions 13 and 14 interposed therebetween), and also an oval shape mathematically defined as a elliptic curve (not shown), and an approximately oval shape comprising two arc portions with a small radius 21 and 22 and two arc portions with a large radius 23 and 24 interposed therebetween and smoothly joined with one another as shown in FIG. 3(b).

Among these oval shapes, in the case of the oval shape containing straight-line portions as shown in FIG. 3(a), a problem peculiar to film-coated tablets such that tablets next to each other are sometimes brought into surface contact with each other at the straight-line portions of the respective tablets in a production process to cause adhesion of films with each other may sometimes arise.

Accordingly, in the scored tablet, a preferred peripheral shape of each of the both surfaces is an oval shape which does not have straight-lines portion such as an oval shape defined as a conic curve, an oval shape shown in FIG. 3(b) and the like.

The oval shape of the peripheral shape of each of the upper and lower surfaces has a preferred range of the ratio S/L of the diameter of the minor axis S to the diameter of the major axis L of the ellipse is from 0.4 to 0.6. If the oval shape has such a ratio, a favorable divisibility can be obtained from the viewpoint that the tablet is easy to hold and a force is easy to apply at the time of dividing. If the ratio S/L is less than 0.4 (that is, the major axis is longer than the diameter of the minor axis S in excess of the specified level), although dividing is easy, the uniformity of half tablets after dividing tends to be decreased, and if the ratio S/L exceeds 0.6 and comes close to 1, the shape is close to a circular shape, and the advantage as the oval shape showing a favorable divisibility is not prominent.

In the case where the ratio S/L is set to 0.4 to 0.6, a specific value of the diameter of the major axis L is from 8 mm to 12 mm. If the value of the diameter of the major axis L is determined, a specific value of the diameter of the minor axis S can be determined from the ratio S/L.

One preferred example of the condition includes a condition in which the major axis is 10 mm, the diameter of the minor axis is 5 mm, and the ratio S/L is 0.5.

In the case where the ratio S/L is set to 0.4 to 0.6, and the diameter of the major axis L is set to 8 mm to 12 mm, a preferred height h of the elevation of each of the both surfaces is from 0.5 mm to 1.5 mm.

Figure 5:
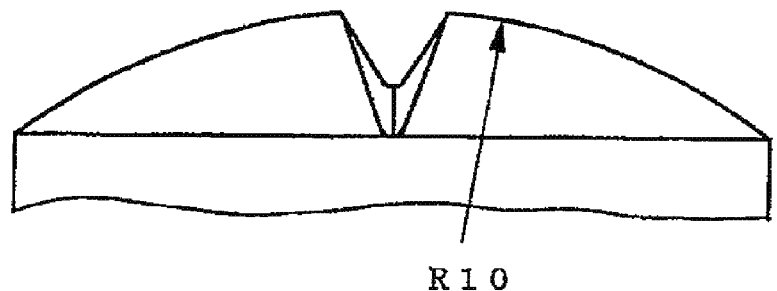
FIG. 5 is a view showing cross-sections along the major axis of preferred forms of elevation of the upper and lower surfaces of the scored tablet.
Figure 5:
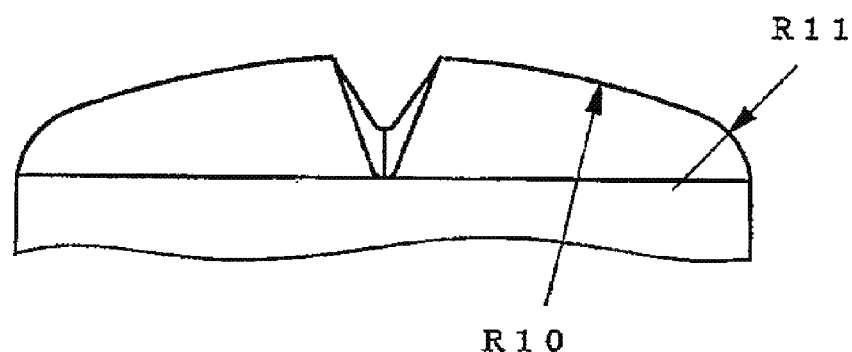
Figure 5:
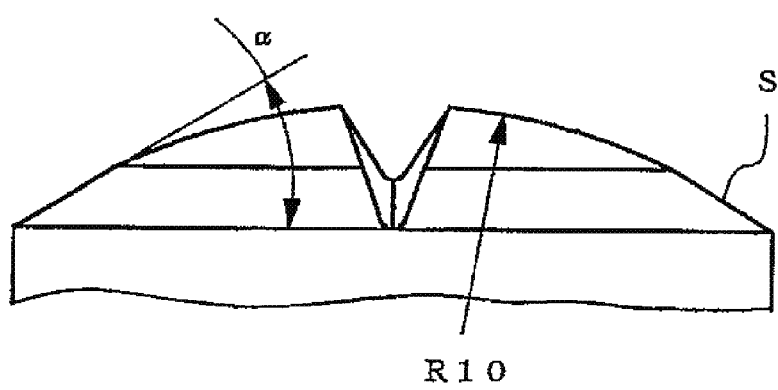

FIG. 5 shows cross-sections along the major axis of preferred forms of elevation of the upper and lower surfaces.

In the embodiment shown in FIG. 5(a), the elevation form is a simple arc in which the elevation level changes from one edge to the other edge through a peak at a constant radius of curvature R10. In the embodiment shown in FIG. 5(b), the elevation form is such that the surface is elevated sharply in edge regions at a small radius of curvature R11 and the elevated manner changes in a peak region to a large radius of curvature R10 (gentle curve). In the embodiment shown in FIG. 5(c), the elevation form is such that the surface is elevated linearly in edge regions and the elevated manner changes in a peak region to a large radius of curvature R10. In this embodiment, the slope surface S in the edge region where the surface is elevated linearly is a curved surface similar to a conical surface or an oval conical surface.

Among these examples of embodiments of elevation forms, the embodiment shown in FIG. 5(c) has an advantage that cracking or chipping of tablets due to contact of tablets with one another is difficult to occur. In this case, a preferred range of an angle of elevation α of the linear elevation in the edge region is from 30° to 40°.

The radius of curvature R10 in the peak region of the cross-section along the major axis in the case where the ratio S/L is set to 0.4 to 0.6, the diameter of the major axis L is set to 8 mm to 12 mm, and the height h of the elevation is set to 0.5 mm to 1.5 mm is preferably from 10 mm to 40 mm. Further, the radius of curvature in the peak region of the cross-section along the minor axis in this case is preferably from 4 mm to 6 mm.

Figure 6:
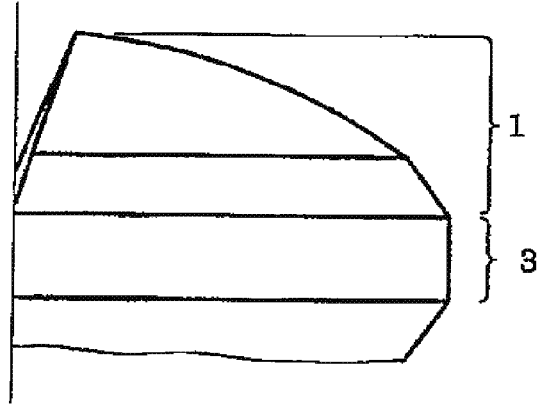
FIG. 6 is a view illustrating embodiments of the peripheral edge portion of the upper surface and the lower surface and the peripheral side surface of the scored tablet.
Figure 6:
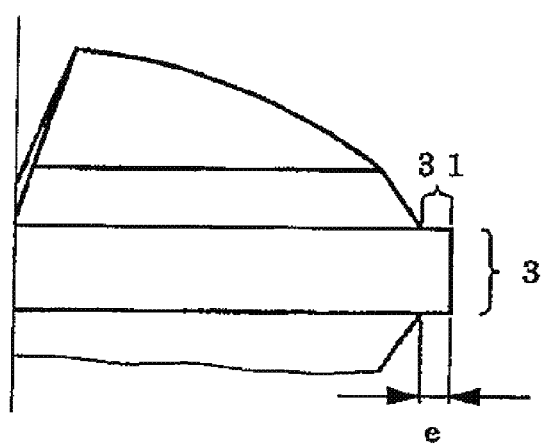
Figure 6:
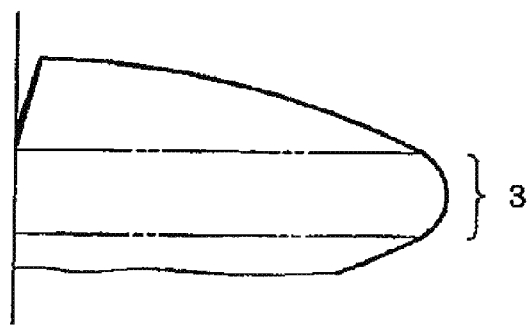

As shown in FIG. 6(a), the elevation of the upper surface and the lower surface may start directly from the boundary line with the peripheral side surface 3, or as shown in FIG. 6(b), an embodiment in which a horizontal flat portion 31 without elevating from the boundary line with the peripheral side surface 3 is formed and the elevation starts from the position slightly inner than the boundary line horizontally to the center may be employed.

When the flat portion is provided, a specific width thereof (the dimension e shown in FIG. 6(b)) in the case where the ratio S/L is set to 0.4 to 0.6, the diameter of the major axis L is set to 8 mm to 12 mm, and the height h of the elevation is set to 0.5 mm to 1.5 mm is preferably from about 0.05 mm to 0.2 mm.

Figure 2:
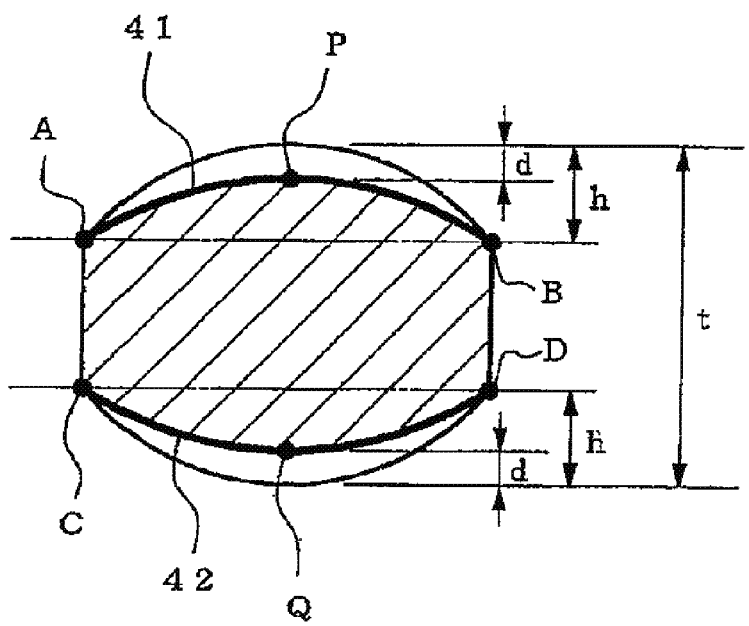
FIG. 2 is a view schematically showing a cross-section when the scored tablet is divided at the score line and how the scored tablet is divided into two.
Figure 2:
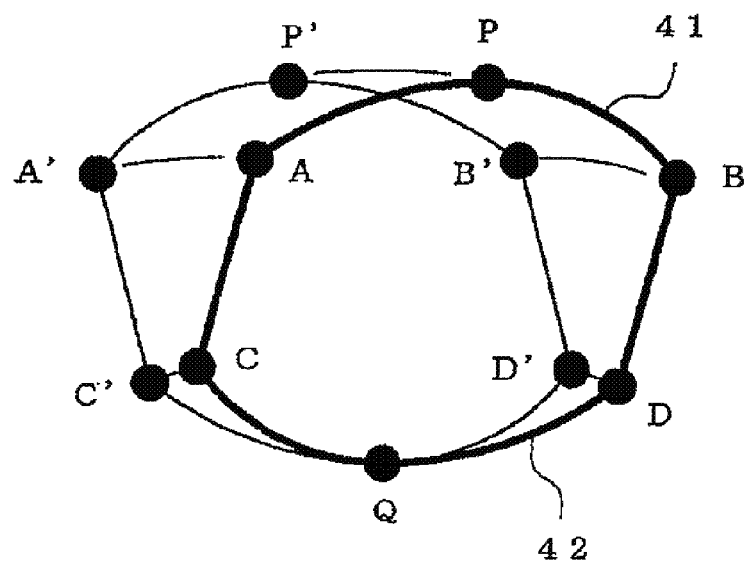

As shown in FIG. 1, FIGS. 6(a) and (b), the peripheral side surface is preferably an oval cylindrical curved surface linearly connecting the peripheral edge of the upper surface to the peripheral edge of the lower surface. If the peripheral side surface is such an oval cylindrical curved surface, when the scored tablet is divided, as described with reference to FIG. 2, ripping of the film more preferably proceeds from the end part of the score line on the upper surface side to the end part of the score line on the lower surface side.

Further, as shown in FIG. 6(c), the peripheral side surface may be a curved surface 31 which is elevated outside and smoothly continuous with the upper and lower surfaces.

Figure 4:
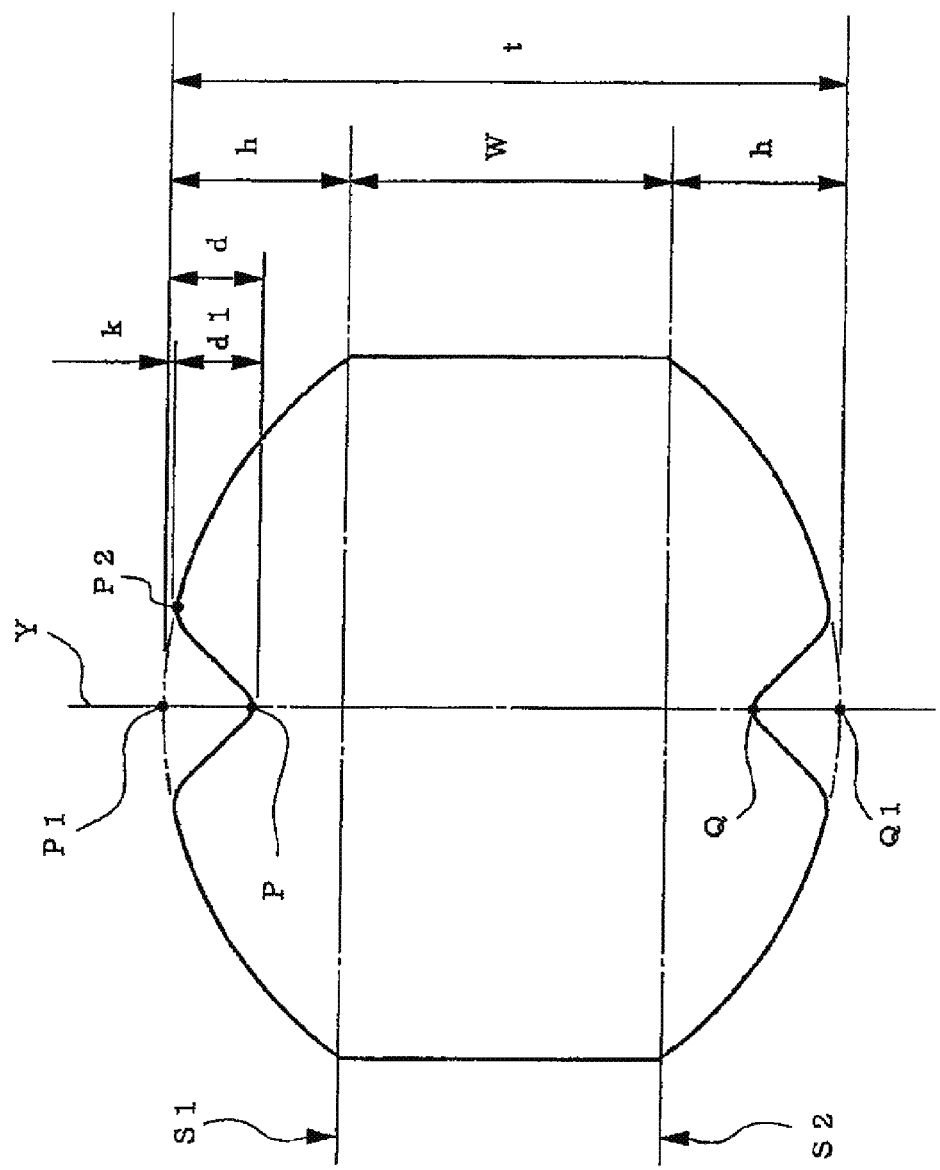
FIG. 4 is a view showing the shape of the cross-section when the scored tablet is cut along the major axis perpendicularly to the minor axis.

The dimension (dimension W in FIG. 4) in the thickness direction of the peripheral side surface is a dimension which constitutes a greater part of the substantial thickness in the total thickness t in the cross-section of the scored tablet divided at the score line and is greatly associated with the bending strength of the scored tablet.

In the case where the ratio S/L is set to 0.4 to 0.6, the diameter of the major axis L is set to 8 mm to 12 mm, and the height h of the elevation is set to 0.5 mm to 1.5 mm, the dimension W in the thickness direction of the peripheral side surface is preferably from about 1 mm to 4 mm, more preferably from 1.5 mm to 3 mm.

Figure 7:
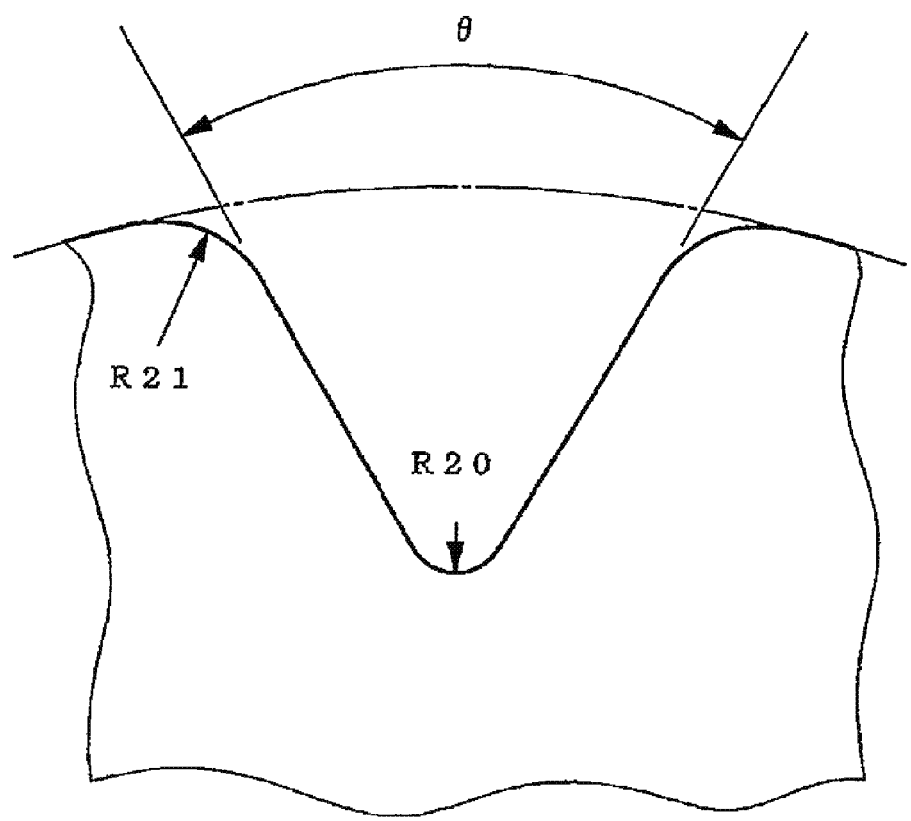
FIG. 7 is a partially enlarged view of the cross-section of the V-shaped groove appearing when the scored tablet is cut with a plane which contains the major axis of the upper surface and is perpendicular to the minor axis thereof.

FIG. 7 is a partially enlarged view of the cross-section of the V-shaped groove appearing when the scored tablet is cut with a plane which contains the major axis of the upper surface and is perpendicular to the minor axis thereof. As shown in the drawing, the shape of the cross-section of the V-shaped groove is substantially a V shape, and as mentioned in the description of advantage, the inner angle θ is from 50° to 90°. From the viewpoint that the film is ripped as intended, the angle θ is more preferably from 55° to 85°, particularly preferably from 60° to 80°. A most preferred example of the inner angle is 70°.

Further, as shown in the drawing, the bottom-most portion of the V shape which is the shape of the cross-section is not formed into a sharp notch tip but is preferably rounded with a moderately small radius R20. The value of this radius R20 is preferably set to about 0.05 mm to 1 mm.

As shown in FIG. 7, it is preferred that the boundary regions between the upper surface and the V-shaped groove (both uppermost portions of the shoulders of the V shape) and/or the boundary regions between the lower surface and the V-shaped groove are rounded with a moderately small radius R21 for the purpose of suppressing cracking, chipping and abrasion of the score line portion during film coating. A preferred value of this radius R21 is from about 0.4 mm to 1.5 mm.

Figure 8:
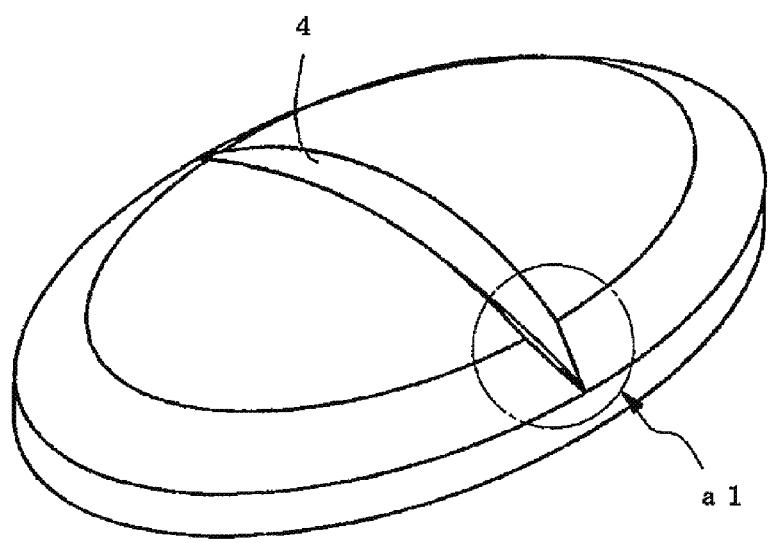
FIG. 8 is a view illustrating the start point of each of the both ends of the V-shaped groove in each of the both surfaces of the scored tablet.
Figure 8:
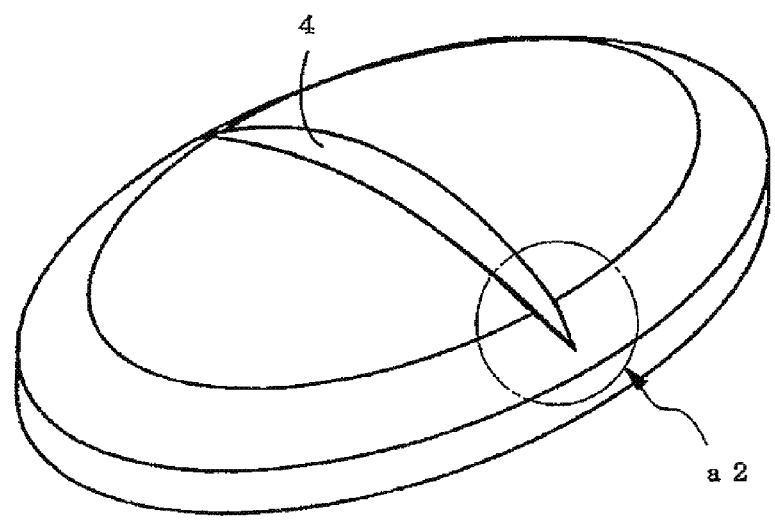

As shown in FIG. 8(a), the start point of each of the both ends of the V-shaped groove in each of the both surfaces may be aligned with the peripheral line (the boundary line with the peripheral side surface) of each of the both surfaces, and further, as shown in FIG. 8(b), the V-shaped groove may start from the position slightly inner than the peripheral line to the center.

As used herein, "path of the bottom of the V-shaped groove" means a line formed by the position of the deepest portion of the V-shaped groove in a cross-sectional view taken along the dividing line of the tablet.

The path of the bottom of the V-shaped groove may be elevated more on the center side than on the peripheral edge sides of each of the upper surface and the lower surface. Hereinafter, the V-shaped groove of the upper surface will be described.

Figure 9:
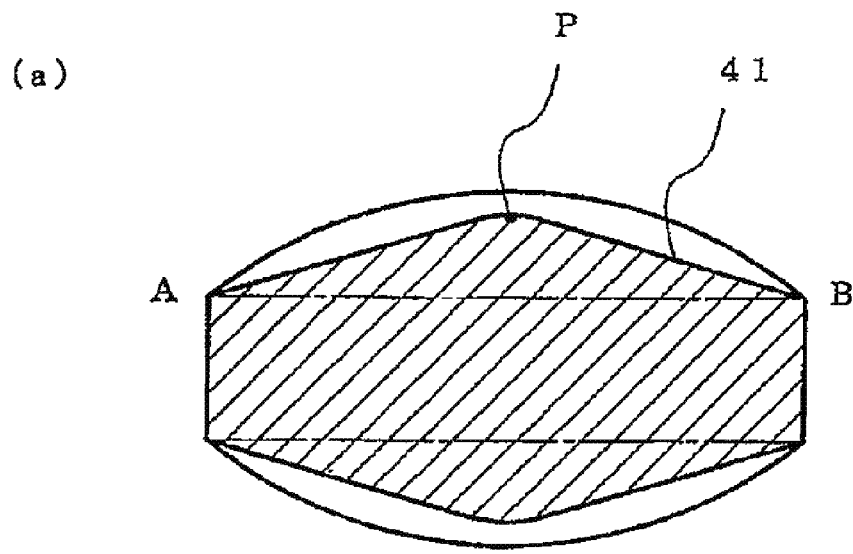
FIG. 9 is a view schematically showing cross-sections when the scored tablet is divided at the score line and a view illustrating elevation patterns of the path of the bottom 41 of the V-shaped groove.
Figure 9:
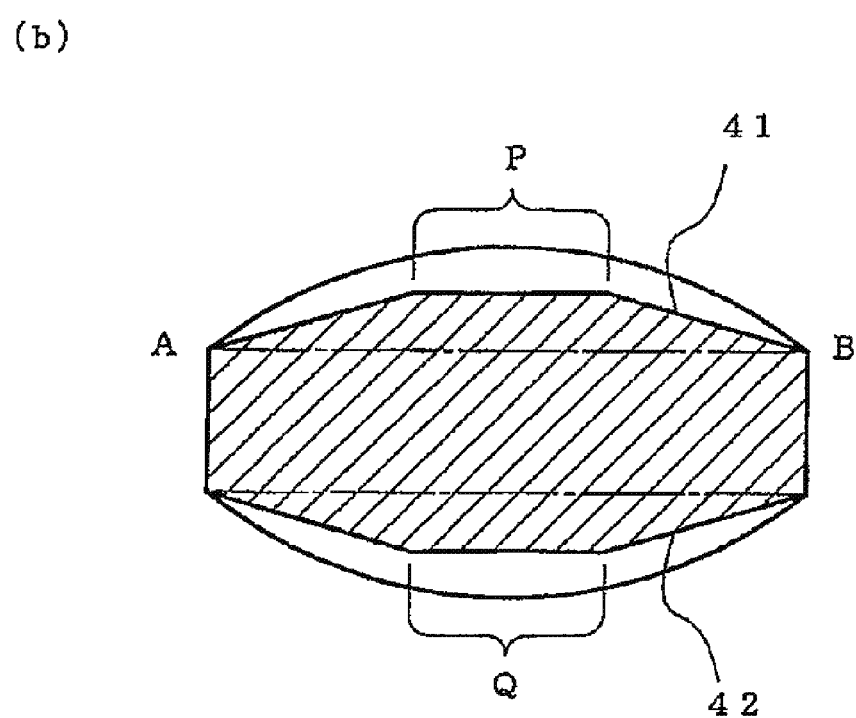
Figure 10:
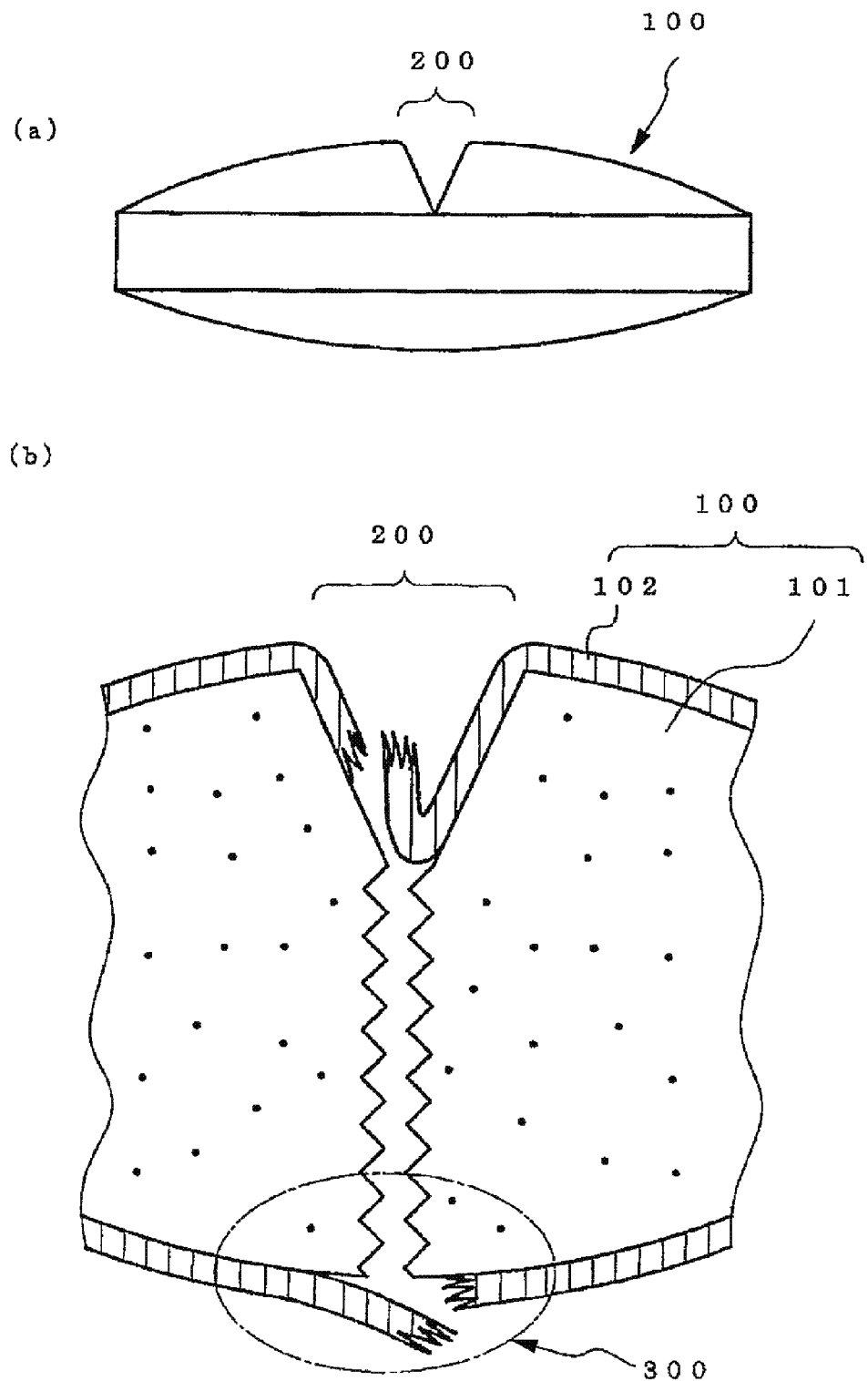
FIG. 10 is an explanatory view showing a problem of a conventional film-coated scored tablet.

In the embodiment shown in FIG. 2(a), the path of the bottom 41 of the V-shaped groove is in the form of a simple arc with a constant radius of curvature throughout the entire length. In the embodiment shown in FIG. 9(a), the path of the bottom 41 of the V-shaped groove is linearly elevated from both end parts A and B to the center part P of the elevation. At the center part P, the path may be sharply pointed or curved and rounded with a small radius. In the embodiment shown in FIG. 9(b), the path of the bottom 41 of the V-shaped groove is linearly elevated from both end parts A and B toward the center part P of the elevation, however, the center part P is not one point peak, but a horizontal linear portion. Other than these, as the line drawn by the path of the bottom of the V-shaped groove, an embodiment which enables the ripping of the film to smoothly proceed such as an embodiment in which the line is elevated with a polygonal shape or an embodiment in which the center portion of the embodiment shown in FIG. 9(b) is combined with the center portion of the embodiment shown in FIG. 2(a) may be selected.

As described in the above-mentioned advantageous effect of the invention, the ratio d/h of the depth d of the V-shaped groove in the center of each of the both surfaces of the scored tablet to the height h of the elevation of the surface is from 0.4 to 1.0 (preferably 0.4 to 0.9).

Further, the ratio 2d/t of a value obtained by doubling the depth d of the V-shaped groove (2d) in the center of each of the both surfaces of the scored tablet to a total thickness t of the scored tablet is from 0.2 to 0.5 (preferably 0.2 to 0.4).

The depth d of the V-shaped groove (in other words, the degree of elevation of the bottom of the V-shaped groove) in the center of each of the both surfaces of the scored tablet may be determined such that the ratio d/h and the ratio 2d/t fall within the proper ranges, respectively, as well as the height h of the elevation of the surface and the dimension W in the thickness direction of the peripheral side surface.

Incidentally, the value of the ratio d/h or the ratio 2d/t is a value in the center of each of the both surfaces of the scored tablet, and in other portions, it may sometimes depart from the range depending on the curved line of the both elevated surfaces or the curved line drawn by the path of the bottom of the V-shaped groove.

In the case where the ratio S/L of the outside diameter of the oval shape is set to 0.4 to 0.6, the diameter of the major axis L is set to 8 mm to 12 mm, the height h of the elevation is set to 0.5 mm to 1.5 mm, and the dimension W in the thickness direction of the peripheral side surface is set to 1.8 mm to 2.3 mm, the depth d of the V-shaped groove in the center is preferably from about 0.5 mm to 0.9 mm, more preferably from 0.6 mm to 0.8 mm. In other words, the degree of elevation of the bottom of the V-shaped groove (height from the reference surface) for obtaining such a depth of the V-shaped groove is from 0.1 mm to 0.5 mm in the center.

A preferred range of the bending strength represented by a force required for dividing the film-coated scored tablet when the force is applied thereto so as to divide the tablet at the score line is [10 N or more and 50 N or less], and a particularly preferred range thereof is [10 N or more and 40 N or less].

If the bending strength is less than 10 N, when the tablet is packaged in a blister pack or the like, when the packaged tablet is transported, or when the tablet is taken out (pushed out) of the package such as a blister pack, the tablet is easily broken. Further, if the bending strength exceeds 50 N, dividing of the tablet is difficult.

The bending strength varies depending on the external shape of the scored tablet, the cross-sectional area appearing when the scored tablet is divided along the score line, the shape of the cross-section of the V-shaped groove serving as the score line, the composition and the content ratios of the contained components of the plain tablet, the compression force and the like. Among these conditions, the external shape of the scored tablet, the cross-sectional area appearing when the scored tablet is divided along the score line and the shape of the cross-section of the V-shaped groove are as defined in the above. Therefore, in order to obtain the above-mentioned appropriate bending strength under such conditions, the composition and the content ratios of the contained components of the plain tablet, the compression force and the like may be suitably determined.

In a test for the bending strength, the tablet is placed on a concave fixture, another fixture with a cutting blade is lowered from above in the vertical direction onto the tip part of the V-shaped groove of the score line portion, and the strength (stress) at the time of dividing the tablet into halves is measured.

The composition of the plain tablet constituting the scored tablet, the composition of the film and the method for producing the same are not particularly limited, and known materials and production method may be used. Preferred configuration examples and production method will be shown below.

The scored tablet can be used for a preparation containing any of various pharmaceutically active ingredients.

Preferred specific examples of such pharmaceutically active ingredients include the following compounds:

1) 2-({6-[(3R)-3-aminopiperidin-1-yl]-3-methyl-2,4-dioxo-3,4-dihydropyrimidin-1(2H)-yl}methyl)benzonitrile (in this description, sometimes abbreviated as "Compound A") or a salt thereof (preferably a benzoate) which is useful as a therapeutic agent for diabetes [for example, type 1 diabetes, type 2 diabetes, type 1.5 diabetes (LADA: latent autoimmune diabetes in adults), gestational diabetes, impaired insulin secretion diabetes, obesity diabetes, impaired glucose tolerance (IGT), impaired fasting glucose (IFG), Impaired fasting glycaemia (IFG), or borderline diabetes] and the like;

2) N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid (in this description, sometimes abbreviated as "Compound B") or a salt thereof which is useful as a therapeutic agent for hyperlipidemia and the like; and 3) 2-ethoxy-1-[[2'-(5-oxo-2,5-dihydro-1,2,4-oxadiazol-3-yl)biphenyl-4-yl]methyl]-1H-benzimidazole-7-carboxylic acid (in this description, sometimes abbreviated as "Compound C") or a salt thereof which is useful as a therapeutic agent for hypertension and the like.

Examples of the salt of the compound include pharmacologically acceptable salts such as a salt with an inorganic acid, a salt with an organic acid and a salt with a basic or acidic amino acid.

Preferred examples of the salt with an inorganic acid include a salt with hydrochloric acid, hydrobromic acid, nitric acid, sulfuric acid, phosphoric acid or the like.

Preferred examples of the salt with an organic acid include a salt with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like.

Preferred examples of the salt with a basic amino acid include a salt with arginine, lysine, ornithine or the like. Preferred examples of the salt with an acidic amino acid include a salt with aspartic acid, glutamic acid or the like.

The scored tablet has a film coating. Materials for film coating include, but not limited to, for example, coating base and coating ingredients. These materials are used an amount which is commonly used in the pharmaceutics formulation area.

Preferred examples of the coating base include a sugar coating base, a water-soluble film coating base, an enteric film coating base and a controlled-release film coating base.

As the sugar coating base, white soft sugar is used, and further, one member or two or more materials selected from talc, precipitated calcium carbonate, gelatin, gum arabic, pullulan and carnauba wax may be used in combination.

Examples of the water-soluble film coating base include a cellulose-based polymer such as hydroxypropyl cellulose (for example, grade: L, SL, SSL (trade name); Nippon Soda Co., Ltd.), hydroxypropylmethyl cellulose (for example, hypromellose 2910 (for example, TC-5 (grade: MW, E, EW, R, RW) (trade name); Shin-Etsu Chemical Co., Ltd.)), hydroxyethyl cellulose or methylhydroxyethyl cellulose; a synthetic polymer such as polyvinyl acetal diethyl aminoacetate, amino alkyl methacrylate copolymer E [Eudragit E (trade name)] or polyvinylpyrrolidone; and a polysaccharide such as pullulan.

Examples of the enteric film coating base include a cellulose-based polymer such as hydroxypropylmethyl cellulose phthalate, hydroxypropylmethyl cellulose acetate succinate, carboxymethylethyl cellulose or cellulose acetate phthalate; an acrylic acid-based polymer such as methacrylic acid copolymer L [Eudragit L (trade name)], methacrylic acid copolymer LD [Eudragit L-30 D-55 (trade name)] or methacrylic acid copolymer S [Eudragit S (trade name)]; a natural product such as shellack.

Examples of the controlled-release film coating base include a cellulose-based polymer such as ethyl cellulose; and an acrylic acid-based polymer such as amino alkyl methacrylate copolymer RS [Eudragit RS (trade name)], an ethyl acrylate-methyl methacrylate copolymer suspension [Eudragit NE (trade name)].

Preferred examples of the coating ingredient include a pigment such as titanium dioxide; a glidant such as talc; a colorant such as iron oxide red or iron oxide yellow; a plasticizer such as polyethylene glycol (for example, macrogol 6000), triethyl citrate, castor oil or polysorbate; and an organic acid such as citric acid, tartaric acid, malic acid or ascorbic acid.

The above materials for film coating may be used by combing two more materials at an appropriate ratio.

The scored tablet may further contain an ingredient commonly used in the pharmaceutical field. Examples of the ingredient include a diluent, a disintegrant, a binder, a lubricant, a colorant, a pH adjusting agent, a surfactant, a stabilizing agent, a sour agent, a flavor, a glidant and the like. These ingredients are used in an amount commonly used in the pharmaceutical field unless otherwise specifically stated.

Examples of the diluent include a sugar or a sugar alcohol such as lactose (for example, lactose monohydrate), fructose, glucose, mannitol or sorbitol; a starch such as corn starch, potato starch, wheat starch, rice starch, partially pregelatinized starch, pregelatinized starch or porous starch; microcrystalline cellulose; anhydrous calcium phosphate, precipitated calcium carbonate, calcium silicate and the like.

In the scored tablet, the diluent is preferably used in an amount to give a content of from 5 to 95% by weight based on 100 parts by weight of the scored tablet of the invention.

As a preferred example of the disintegrant, carboxymethyl cellulose, carboxymethyl cellulose calcium, carboxymethyl starch sodium, croscarmellose sodium, carmellose calcium, crospovidone, low-substituted hydroxypropyl cellulose, hydroxypropyl starch or the like is used. The used amount of the disintegrant is an amount to give a content of from 0.5 to 25 parts by weight based on 100 parts by weight of the scored tablet of the invention.

Preferred examples of the binder include hydroxypropyl cellulose (for example, grade: L, SL, SSL (trade name); Nippon Soda Co., Ltd.), hydroxypropylmethyl cellulose (for example, hypromellose 2910 (for example, TC-5 (grade: MW, E, EW, R, RW) (trade name); Shin-Etsu Chemical Co., Ltd.)), polyvinylpyrrolidone (povidone), gum arabic and the like.

In the scored tablet, the binder is preferably used in an amount to give a content of from 1 to 20% by weight based on 100 parts by weight of the scored tablet of the invention.

Preferred examples of the lubricant include magnesium stearate, calcium stearate, talc, sucrose fatty acid ester, sodium stearyl fumarate and the like. The used amount of the lubricant is an amount to give a content of from 0.5 to 2% by weight based on 100 parts by weight of the solid preparation.

Preferred examples of the colorant include a food dye (for example, food yellow No. 5, food red No. 2, food blue No. 2), a food lake color, iron oxide red, iron oxide yellow and the like.

Preferred examples of the pH adjusting agent include citrate, phosphate, carbonate, tartrate, fumarate, acetate and amino acid salt.

Preferred examples of the surfactant include sodium lauryl sulfate, polysorbate 80, polyoxyethylene (160) polyoxypropylene (30) glycol and the like.

Preferred examples of the stabilizing agent include tocopherol, tetrasodium edetate, nicotinamide, a cyclodextrin and the like.

Preferred examples of the sour agent include ascorbic acid, citric acid, tartaric acid and malic acid.

Preferred examples of the flavor include menthol, Mentha oil, lemon oil and vanillin.

Preferred examples of the glidant include colloidal silicon dioxide, aqueous silicon dioxide and talc.

The above ingredients may be used by combining two or more members at an appropriate ratio.

The scored tablet of the invention can be produced according to the following production steps. Each starting material in the following production steps is used in an amount to give the above-mentioned content per finally obtained tablet.

1) A granule is produced by granulating a pharmaceutically active ingredient, a diluent and a binder. Specifically, a pharmaceutically active ingredient and a diluent (for example, lactose monohydrate, mannitol, corn starch or microcrystalline cellulose) are uniformly mixed in a fluid bed granulator, and the resulting mixture is granulated while spraying a dispersion of a binder (for example, hydroxypropyl cellulose or polyvinylpyrrolidone (povidone)) in a solvent (for example, water, acetone, ethyl alcohol, propyl alcohol, or a mixture thereof at an appropriate ratio). Subsequently, the resulting granules are dried and the obtained granules are milled, whereby milled granules are obtained.

2) To the obtained milled granules, a disintegrant (for example, croscarmellose sodium, carmellose calcium, low-substituted hydroxypropyl cellulose or carboxymethyl starch) and a lubricant (for example, magnesium stearate), and if necessary, further a diluent (for example, microcrystalline cellulose) are added and all the ingredients are blended, whereby blended granules for compressing are prepared.

3) The resulting granules are compressed with a tablet press having a punch with a score line, whereby plain tablets are obtained.

4) Onto the obtained plain tablet, a film coating liquid is sprayed in a pan coating equipment, whereby film-coated tablets are obtained.

Incidentally, the above-mentioned dispersion may be either a solution or a suspension, and the "dispersion" as used herein includes both solution and suspension.

The scored tablet of the invention may be debossed or printed with letters for identification.

In the above-mentioned production steps, the operations such as blending, compressing and film coating are performed according to a method commonly used in the technical field of pharmaceutical preparations.

The blending is performed, for example, using a mixer such as a V-blender or a diffusion mixer; and a granulator such as a high-shear wet granulator, a fluid bed granulator, an extrusion granulator or a roller compactor.

The compression is performed, for example, using a single punch tablet press, a rotary tablet press or the like.

When a single punch tablet press, a rotary tablet press or the like is used, a compression force of generally from 1 to 45 $kN/cm^2$ (preferably from 5 to 40 $kN/cm^2$) is preferably employed. Further, for the purpose of preventing capping, it is preferred to use a tapered die.

The film coating is performed, for example, using a pan coating equipment or the like.

As the materials of the coating film formed on the surface of the plain tablet, the same materials can be used.

The film coating layer is formed at a proportion of generally from 1 to 10 parts by weight, preferably from 2 to 6 parts by weight based on 100 parts by weight of the plain tablet.

The scored tablet can be widely used in the field of food, quasi drug and the like other than the pharmaceutical preparation.

The scored tablet of the invention can be safely administered orally or parenterally to a mammal (e.g., mouse, rat, rabbit, cat, dog, bovine, horse, monkey, human).

The dose of the scored tablet of the invention only needs to contain an effective amount of a pharmaceutically active ingredient.

The present invention is explained in more detail in the following by referring to Example, Reference Example, Comparative Example and Experimental Examples, which are not to be construed as limitative.

As ingredients for pharmaceutical preparations in the following Examples, Reference Example, Comparative Example and Examples, the Japanese Pharmacopoeia 15th edition, the Japanese Pharmaceutical Codex or Japanese Pharmaceutical Excipients 2003 compatible products were used.

EXAMPLES

Hereinafter, preferred specific examples of the invention will be described.

Example 1

In this example, from the above-mentioned forms and dimensions of the respective parts, the following conditions were selected and combined, and the scored tablets were actually produced.

Forms and Dimensions of Respective Parts

The tolerance of the dimension of the punch to be used in the tablet press is from −0.01 mm to −0.05 mm, and the acceptance of the dimension of the die is from +0.01 mm to +0.03 mm.

Peripheral shape of both surfaces of the scored tablet: as shown in FIG. 3(b), an approximately oval shape in which two arc portions with a large radius (radius: 11.25 mm) are interposed between two arc portions with a small radius (radius: 2 mm) and smoothly joined with one another.

Diameter of the major axis L of the oval shape: 10 mm; diameter of the minor axis S: 5 mm; ratio S/L: 0.5

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 0.687 mm Elevation pattern of path of bottom of V-shaped groove: elevation in the form of an arc with a radius of 14.751 mm throughout the entire length.

Depth of V-shaped groove in the center part (dimension d in FIG. 4): 0.61 mm, ratio d/h: 0.89

Dimension in the thickness direction of peripheral side surface (dimension W in FIG. 4): 1.926 mm Total thickness (dimension t in FIG. 4): 3.3 mm, ratio 2d/t: 0.37

Inner angle of V shape being the shape of cross-section of V-shaped groove: 70°

Production of the Scored Tablet

In a fluid bed granulator (FD-WSG-60, Powrex Corporation), according to the formulation shown in Table 1 and the amount of charge shown in Table 2, a benzoate of Compound A, mannitol and microcrystalline cellulose were uniformly mixed, and the resulting mixture was granulated in the machine by spraying an aqueous solution in which hydroxypropyl cellulose was dissolved and the resulting granules were dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, microcrystalline cellulose, croscarmellose sodium and magnesium stearate were added, and all the ingredients were blended in a diffusion mixer (TM-400S, Showa Kagaku Kikai Kosakusho Co., Ltd.), whereby blended granules for compression were prepared.

The resulting blended granules were compressed by a rotary tablet press (AQUA0836SS2JII, Kikusui Seisakusho, Ltd.) using an oval punch having a diameter of a major axis of 10.0 mm and a diameter of a minor axis of 5.0 mm (S/L=0.5) with a score line in the form shown in Table 1 at a compression force level of from 9.5 to 11.9 kN/punch to give a plain tablet having a weight of 150 mg and a thickness of 3.3 mm, whereby the plain tablet was obtained.

In a pan coating equipment (DRC-1200, Powrex Corporation), a hypromellose 2910 solution in which titanium dioxide and iron oxide yellow or iron oxide red were dispersed was sprayed onto the obtained plain tablet, and further subsequently, a macrogol 6000 solution was sprayed thereonto, whereby film-coated tablets having a score line on both surfaces containing Compound A (free form) in an amount of 6.25 mg, 12.5 mg and 25 mg per tablet were obtained.

TABLE 1

| | | Dose | | |
|---|---|---|---|---|
| | | 6.25 mg | 12.5 mg | 25 mg |
| Plain tablet | | | | |
| Component (A) | Compound A (benzoate) | 8.50 mg | 17.00 mg | 34.00 mg |
| | Mannitol | 105.20 mg | 96.70 mg | 79.70 mg |
| | Microcrystalline cellulose | 15.00 mg | 15.00 mg | 15.00 mg |
| | Hydroxypropyl cellulose | 4.50 mg | 4.50 mg | 4.50 mg |
| Component (B) | Microcrystalline cellulose | 7.50 mg | 7.50 mg | 7.50 mg |
| | Croscarmellose sodium | 7.50 mg | 7.50 mg | 7.50 mg |
| | Magnesium stearate | 1.80 mg | 1.80 mg | 1.80 mg |
| Film coating | Hypromellose 2910 | 5.340 mg | 5.388 mg | 5.340 mg |
| | Titanium dioxide | 0.60 mg | 0.60 mg | 0.60 mg |
| | Iron oxide yellow | — mg | 0.012 mg | 0.06 mg |
| | Iron oxide red | 0.06 mg | — mg | — mg |
| | Macrogol 6000 | 0.1 mg | 0.1 mg | 0.1 mg |
| | Total | 156.10 mg | 156.10 mg | 156.10 mg |
| Form of score line | Depth of V-shaped groove (d) | 0.61 mm | 0.61 mm | 0.61 mm |
| | Height of elevation of surface of each of upper surface and lower surface (h) | 0.687 mm | 0.687 mm | 0.687 mm |
| | d/h | 0.89 | 0.89 | 0.89 |
| | Inner angle of V shape of V-shaped groove | 70° | 70° | 70° |
| Total thickness of plain tablet (t) | | 3.3 mm | 3.3 mm | 3.3 mm |
| | 2d/t | 0.37 | 0.37 | 0.37 |

TABLE 2

| | | Dose | | |
|---|---|---|---|---|
| | | 6.25 mg | 12.5 mg | 25 mg |
| Plain tablet | | | | |
| Component (A) | Hydroxypropyl cellulose | 2025 g | 2025 g | 2025 g |
| | Purified water | 31725 g | 31725 g | 31725 g |
| | Compound A (benzoate) | 3825 g | 7650 g | 15300 g |

TABLE 2-continued

| | | Dose | | |
|---|---|---|---|---|
| | | 6.25 mg | 12.5 mg | 25 mg |
| Component (B) | Mannitol | 47340 g | 43515 g | 35865 g |
| | Microcrystalline cellulose | 6750 g | 6750 g | 6750 g |
| | Microcrystalline cellulose | 3375 g | 3375 g | 3375 g |
| | Croscarmellose sodium | 3375 g | 3375 g | 3375 g |
| | Magnesium stearate | 810.0 g | 810.0 g | 810.0 g |
| Film coating | Hypromellose 2910 | 4007 g | 4043 g | 4007 g |
| | Titanium dioxide | 450.2 g | 450.2 g | 450.2 g |
| | Iron oxide yellow | — g | 9.004 g | 45.02 g |
| | Iron oxide red | 45.02 g | — g | — g |
| | Purified water | 40523 g | 40523 g | 40523 g |
| | Macrogol 6000 | 1842 g | 1842 g | 1842 g |
| | Purified water | 16580 g | 16580 g | 16580 g |

Reference Example

In this Reference example, from the above-mentioned forms and dimensions of the respective parts, a combination other than the embodiment shown in Example 1 was selected, and a plain tablet of the scored tablet was actually produced by the same production process as in the above-mentioned Example 1. The forms and dimensions of the respective parts are as follows.

[Forms and Dimensions of Respective Parts]

The tolerance of the dimension of the punch to be used in the tablet press is from −0.01 mm to −0.05 mm, and the acceptance of the dimension of the die is from +0.01 mm to +0.03 mm.

Peripheral shape of both surfaces of a plain tablet of the scored tablet: as shown in FIG. 3(b), an oval shape in which two arc portions with a large radius (radius: 11.25 mm) are interposed between two arc portions with a small radius (radius: 2 mm) and smoothly joined with one another.

Diameter of the major axis L of the oval shape: 10 mm; diameter of the minor axis S: 5 mm; ratio S/L: 0.5

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 0.687 mm Elevation pattern of path of bottom of V-shaped groove: elevation in the form of an arc with a radius of 14.751 mm throughout the entire length.

Depth of V-shaped groove in the center part (dimension d in FIG. 4): 0.61 mm, ratio d/h: 0.89

Dimension in the thickness direction of peripheral side surface (dimension W in FIG. 4): 1.926 mm Total thickness (dimension t in FIG. 4): 3.3 mm, ratio 2d/t: 0.37

Inner angle of V shape being the shape of cross-section of V-shaped groove: 70°

Production of a Plain Tablet of the Scored Tablet

In a fluid bed granulator (FD-WSG-60, Powrex Corporation), according to the formulation shown in Table 1 and the amount of charge shown in Table 2, a benzoate of Compound A, mannitol and microcrystalline cellulose were uniformly mixed, and the resulting mixture was granulated in the machine by spraying an aqueous solution in which hydroxypropyl cellulose was dissolved and the resulting granules were dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, microcrystalline cellulose, croscarmellose sodium and magnesium stearate were added, and all the ingredients were blended in a diffusion mixer (TM-400S, Showa Kagaku Kikai Kosakusho Co., Ltd.), whereby blended granules for compression were prepared.

The resulting blended granules were compressed by a rotary tablet press (AQUA0836SS2JII, Kikusui Seisakusho, Ltd.) using an oval punch having a diameter of a major axis of 10.0 mm and a diameter of a minor axis of 5.0 mm (S/L=0.5) with a score line in the form shown in Table 1 at a compression force level of from 6, 9, 12, or 18 kN/punch to give a plain tablet having a weight of 150 mg, whereby the plain tablets containing Compound A (free form) in an amount of 6.25 mg, 12.5 mg and 25 mg per tablet were obtained at each of the compression force levels.

Example 2

In this example, from the above-mentioned forms and dimensions of the respective parts, a preferred combination other than the embodiments shown in Examples 1 and Reference Example was selected, and the scored tablet was actually produced by the same production process as in the above-mentioned Example 1. The forms and dimensions of the respective parts are as follows.

[Forms and Dimensions of Respective Parts]

The tolerance of the dimension of the punch to be used in the tablet press is from −0.01 mm to −0.05 mm, and the acceptance of the dimension of the die is from +0.01 mm to +0.03 mm.

Peripheral shape of both surfaces of the scored tablet: as shown in FIG. 3(b), an approximately oval shape in which two arc portions with a large radius (radius: 10 mm) are interposed between two arc portions with a small radius (radius: 2.719 mm) and smoothly joined with one another.

Diameter of the major axis L of the oval shape: 12 mm; diameter of the minor axis S: 7 mm; ratio S/L: 0.58

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 1.3 mm Elevation pattern of path of bottom of V-shaped groove: elevation in the form of an arc with a radius of 11.81 mm throughout the entire length.

Depth of V-shaped groove in the center part (dimension d in FIG. 4): 0.8 mm, ratio d/h: 0.62

Dimension in the thickness direction of peripheral side surface (dimension W in FIG. 4): 2 mm Total thickness (dimension t in FIG. 4): 4.6 mm, ratio 2d/t: 0.35

Inner angle of V shape being the shape of cross-section of V-shaped groove: 70°

Production of the Scored Tablet

In a fluid bed granulator (FD-WSG-60, Powrex Corporation), according to the formulation shown in Table 3 and the amount of charge shown in Table 4, Compound B, lactose monohydrate and corn starch were uniformly mixed, and the resulting mixture was granulated in the machine by spraying an aqueous solution in which hydroxypropyl cellulose was dissolved and the resulting granule was dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, carmellose calcium and magnesium stearate were added, and all the ingredients were blended in a diffusion mixer (TM-400S, Showa Kagaku Kikai Kosakusho Co., Ltd.), whereby blended granules for compression were prepared.

The resulting blended granules were compressed by a rotary tablet press (Correct 19K, Kikusui Seisakusho, Ltd.) using an oval punch having a diameter of a major axis of 12.0 mm and a diameter of a minor axis of 7.0 mm (S/L=0.58) with a score line in the form shown in the column "Punch 3" of Table 6 at a compression force level of 8 kN/punch to give a plain tablet having a weight of 300 mg and a thickness of 4.6 mm, whereby the plain tablets were obtained. In a pan coating equipment (Hicoater HCP-75, Freund Corporation), according to the amount of charge shown in Table 5, a liquid in which hypromellose 2910 and macrogol 6000 were dissolved and titanium dioxide was dispersed was sprayed onto the obtained plain tablets, and further subsequently, a macrogol 6000 solution was sprayed thereonto, whereby film-coated tablets having a score line on both surfaces containing Compound B in an amount of 50 mg per tablet were obtained.

TABLE 3

| | | Dose 50 mg |
|---|---|---|
| Plain tablet | | |
| Component (A) | Compound B | 50.00 mg |
| | Lactose monohydrate | 164.00 mg |
| | Corn starch | 60.00 mg |
| | Hydroxypropyl cellulose | 9.00 mg |
| Component (B) | Carmellose calcium | 15.00 mg |
| | Magnesium stearate | 2.00 mg |
| Film coating | Hypromellose 2910 | 7.50 mg |
| | Macrogol 6000 | 1.50 mg |
| | Titanium dioxide | 1.00 mg |
| | Macrogol 6000 | 0.125 mg |
| | Total | 310.125 mg |

TABLE 4

| Plain tablet | | |
|---|---|---|
| Component (A) | Hydroxypropyl cellulose | 2302 g |
| | Purified water | 43740 g |
| | Compound B | 11400 g |
| | Lactose monohydrate | 37390 g |
| | Corn starch | 13680 g |
| Component (B) | Carmellose calcium | 3210 g |
| | Magnesium stearate | 428.0 g |

TABLE 5

| Film coating | Hypromellose 2910 | 75 g |
|---|---|---|
| | Macrogol 6000 | 15 g |
| | Titanium dioxide | 10 g |

TABLE 5-continued

| | Purified water | 900 g |
|---|---|---|
| | Macrogol 6000 | 1 g |
| | Purified water | 99 g |

TABLE 6

| | | Punch 1 | Punch 2 | Punch 3 | Punch 4 |
|---|---|---|---|---|---|
| Form of score line | Depth of V-shaped groove (d) | 0.4 mm | 0.6 mm | 0.8 mm | 1.3 mm |
| | Height of elevation of surface of each of upper surface and lower surface (h) | 1.3 mm | 1.3 mm | 1.3 mm | 1.3 mm |
| | d/h | 0.31 | 0.46 | 0.62 | 1.00 |
| | Inner angle of V shape of V-shaped groove | 100° | 70° | 70° | 100° |

Example 3

In this example, from the above-mentioned forms and dimensions of the respective parts, a preferred combination other than the embodiments shown in Examples 1 and 2 and Reference Examples was selected, and the scored tablet was actually produced by the same production process as in the above-mentioned Example 1. The forms and dimensions of the respective parts are as follows.

[Forms and Dimensions of Respective Parts]

The tolerance of the dimension of the punch to be used in the tablet press is from −0.01 mm to −0.05 mm, and the acceptance of the dimension of the die is from +0.01 mm to +0.03 mm.

Peripheral shape of both surfaces of the scored tablet: as shown in FIG. 3(b), an approximately oval shape in which two arc portions with a large radius (radius: 10 mm) are interposed between two arc portions with a small radius (radius: 2.719 mm) and smoothly joined with one another.

Diameter of the major axis L of the oval shape: 12 mm; diameter of the minor axis S: 7 mm; ratio S/L: 0.58

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 1.3 mm Elevation pattern of path of bottom of V-shaped groove: elevation in the form of an arc with a radius of 11.81 mm throughout the entire length.

Depth of V-shaped groove in the center part (dimension d in FIG. 4): 0.6 mm, ratio d/h: 0.46

Dimension in the thickness direction of peripheral side surface (dimension W in FIG. 4): 2 mm Total thickness (dimension t in FIG. 4): 4.6 mm, ratio 2d/t: 0.26

Inner angle of V shape being the shape of cross-section of V-shaped groove: 70°

Production of the Scored Tablet

In a fluid bed granulator (FD-5S, Powrex Corporation), according to the formulation shown in Table 3 and the amount of charge shown in Table 7, Compound B, lactose monohydrate and corn starch were uniformly mixed, and the resulting mixture was granulated in the machine by spraying an aqueous solution in which hydroxypropyl cellulose was dissolved and the resulting granule was dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, carmellose calcium and magnesium stearate were added, and all the ingredients were blended in a diffusion mixer (TM-15, Showa Kagaku Kikai Kosakusho Co., Ltd.), whereby blended granules for compression were prepared.

The resulting blended granules were compressed by a rotary tablet press (Correct 19K, Kikusui Seisakusho, Ltd.) using an oval punch having a diameter of a major axis of 12.0 mm and a diameter of a minor axis of 7.0 mm (S/L=0.58) with a score line in the form shown in the column "Punch 2" of Table 6 at a compression force level of 8 kN/punch to give a plain tablet having a weight of 300 mg and a thickness of 4.6 mm, whereby the plain tablet was obtained.

In a pan coating equipment (Hicoater HCP-75, Freund Corporation), according to the amount of charge shown in Table 5, a liquid in which hypromellose 2910 and macrogol 6000 were dissolved and titanium dioxide was dispersed was sprayed onto the obtained plain tablet, and further subsequently, a macrogol 6000 solution was sprayed thereonto, whereby film-coated tablets having a score line on both surfaces containing Compound B in an amount of 50 mg per tablet were obtained.

TABLE 7

| Plain tablet | | |
|---|---|---|
| Component (A) | Hydroxypropyl cellulose | 148.5 g |
| | Purified water | 2822 g |
| | Compound B | 833.3 g |
| | Lactose monohydrate | 2698 g |
| | Corn starch | 990.0 g |
| Component (B) | Carmellose calcium | 210.0 g |
| | Magnesium stearate | 28.00 g |

Example 4

In this example, the following conditions were selected from the above-described forms and dimensions of the respective parts and combined, and the scored tablets were actually produced.

[Forms and Dimensions of Respective Parts]

The tolerance of the dimension of a punch to be used in a tablet press is from −0.01 mm to −0.05 mm. The acceptance of the dimension of a die is from +0.01 mm to +0.03 mm.

10 mg Tablet:

Peripheral shape of both surfaces of the scored tablet: as shown in FIG. 3(b), an approximately oval shape in which two arc portions with a large radius (radius: 7.403 mm) are interposed between two arc portions with a small radius (radius: 1.8 mm) and smoothly jointed with one another.

Diameter of the major axis L of the oval shape: 8.0 mm, diameter of the minor axis S: 4.5 mm, and ratio S/L: 0.56

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 0.61 mm Elevation pattern of path of bottom of V-shaped groove: elevation in the form of an arc with a radius of 33.31 mm throughout the entire length.

Depth of the V-shaped groove in the center part (dimension d in FIG. 4): 0.54 mm, ratio d/h: 0.89

Dimension in the thickness direction of peripheral side surface (dimension W in FIG. 4): 1.78 mm Total thickness (dimension t in FIG. 4): 3.0 mm, ratio 2d/t: 0.36

Inner angle of V shape being the shape of cross-section of V-shaped groove: 70°

20 mg Tablet and 40 mg Tablet:

Peripheral shape of both surfaces of the scored tablet: as shown in FIG. 3(b), an approximately oval shape in which two arc portions with a large radius (radius: 8.5 mm) are interposed between two arc portions with a small radius (radius: 2 mm) and smoothly jointed with one another.

Diameter of the major axis L of the oval shape: 9 mm, diameter of the minor axis S: 5 mm, and ratio S/L: 0.56

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 0.687 mm Elevation pattern of path of bottom of V-shaped groove: elevation in the form of an arc with a radius of 18.634 mm throughout the entire length.

Depth of the V-shaped groove in the center part (dimension d in FIG. 4): 0.65 mm, ratio d/h: 0.95

Dimension in the thickness direction of peripheral side surface (dimension W in FIG. 4): 1.826 mm Total thickness (dimension t in FIG. 4): 3.2 mm, ratio 2d/t: 0.41

Inner angle of V shape being the shape of cross-section of V-shaped groove: 70°

Production of the Scored Tablet 10 mg Tablet:

In a fluid bed granulator (FD-WSG-60, Powrex Corporation), according to the formulation shown in Table 8 and the amounts of charge shown in Table 9, Compound C, lactose monohydrate and corn starch were uniformly mixed, and the resulting mixture was granulated in the machine by spraying an aqueous solution in which hydroxypropyl cellulose and Macrogol 6000 were dissolved and the resulting granule was dried therein.

The obtained granules were milled using a screening mill (P-7S, Showa Kagaku Kikai Kousakusho) with a punching screen having holes with an inner diameter of 1.5 mm.

To the resulting milled granules, low substituted hydroxypropyl cellulose and magnesium stearate were added, and all the ingredients were blended in a diffusion mixer (TM-400S, Showa Kagaku Kikai Kousakusho), whereby blended granules for compression were prepared.

The resulting blended granules were compressed using by a rotary tablet press (AQUA0836SS2JII, Kikusui Seisakusho Ltd.) using an oval punch having a diameter of a major axis of 8.0 mm and a diameter of a minor axis of 4.5 mm (S/L=0.56) with a score line in the form shown in Table 8 at a compression force level of 10.0 kN/punch to give a plain tablet having a weight of 100 mg and the thickness of 3.0 mm, whereby the plain tablets were obtained.

In a pan coating equipment (DRC-1200, Powrex Corporation), a hypromellose 2910 (TC-5R, Shin-Etsu Chemical Co. Ltd.) solution containing Macrogol 6000 in which titanium dioxide, iron oxide yellow and iron oxide red were dispersed was sprayed onto the obtained plain tablets, and further subsequently, a macrogol 6000 solution was sprayed thereonto, whereby film-coated tablets having a score line on both surfaces containing Compound C in an amount of 10 mg per tablet were obtained.

20 mg Tablet:

In a fluid bed granulator (FD-WSG-60, Powrex), according to the formulation shown in Table 8 and the amounts of charge shown in Table 9, Compound C, lactose monohydrate and corn starch were uniformly mixed and the resulting mixture was granulated in the machine by spraying an aqueous solution in which hydroxypropyl cellulose and macrogol 6000 were dissolved, and the resulting granules were dried therein.

The obtained granules were milled using a screening mill (P-7S, Showa Kagaku Kikai Kousakusho Co., Ltd.) with a punching screen having holes with an inner diameter of 1.5 mm.

To the resulting milled granules, low substituted hydroxypropyl cellulose, microcrystalline cellulose and magnesium stearate were added, and all the ingredients were blended in a diffusion mixer (TM-400S, Showa Kagaku Kikai Kousakusho Co., Ltd.), whereby blended granules for compression were prepared.

The resulting blended granules were compressed by a rotary tablet press (AQUA0836SS2JII, Kikusui Seisakusho Ltd.) and an oval punch having a diameter of a major axis of 9.0 mm and a diameter of a minor axis of 5.0 mm (S/L=0.56) with a score line in the form shown in Table 8 at a compression force level of 10.6 kN/punch to give a plain tablet having a weight of 130 mg and a thickness of 3.2 mm, whereby the plain tablets were obtained.

In a pan coating equipment (DRC-1200, Powrex Corporation), a hypromellose 2910 (TC-5E, Shin-Etsu Chemical Co. Ltd.) solution containing macrogol 6000 in which titanium dioxide and iron oxide red were dispersed was sprayed onto the obtained plain tablet, and further subsequently, a macrogol 6000 solution was sprayed thereonto, whereby film-coated tablets having a score line on both surfaces containing Compound C in an amount of 20 mg per tablet were obtained.

40 mg Tablet:

In a fluid bed granulator (FD-WSG-60, Powrex Corporation), according to the formulation shown in Table 8 and the amounts of charge shown in Table 9, Compound C, lactose monohydrate, corn starch and microcrystalline cellulose were uniformly mixed, and the resulting mixture was granulated in the machine by spraying an aqueous solution in which hydroxypropyl cellulose and macrogol 6000 were dissolved and the resulting granules were dried therein.

The obtained granules were milled using a screening mill (P-7S, Showa Kagaku Kikai Kousakusho Co., Ltd.) with a punching screen having holes with an inner diameter of 1.5 mm.

To the resulting milled granules, low substituted hydroxypropyl cellulose, microcrystalline cellulose and magnesium stearate were added, and all the ingredients were blended in a diffusion mixer (TM-400S, Showa Kagaku Kikai Kousakusho Co., Ltd.), whereby blended granules for compression were prepared.

The resulting blended granules were compressed by a rotary tablet press (AQUA0836SS2JII, Kikusui Seisakusho Ltd.) using an oval punch having a diameter of a major axis of 9.0 mm and a diameter of a minor axis of 5.0 mm (S/L=0.56) with a score line in the form shown in Table 8 at a compression force level of 11.0 kN/punch to give a plain tablet having a weight of 130 mg and a thickness of 3.2 mm, whereby the plain tablets were obtained.

In a pan coating equipment (DRC-1200, Powrex Corporation), a Hypromellose 2910 (TC-5E, Shin-Etsu Chemical Co. Ltd.) solution containing macrogol 6000 in which titanium dioxide and iron oxide yellow were dispersed was sprayed onto the obtained plain tablet, and further subsequently, a macrogol 6000 solution was sprayed thereonto, whereby film-coated tablet having a score line on both surfaces containing Compound C in an amount of 40 mg per tablet were obtained.

TABLE 8

| | | Dosage | | |
|---|---|---|---|---|
| | | 10 mg | 20 mg | 40 mg |
| Uncoated tablet | | | | |
| Component (A) | Compound C | 10 mg | 20 mg | 40 mg |
| | Lactose monohydrate | 51 mg | 53.9 mg | 29.3 mg |
| | Corn starch | 23 mg | 20 mg | 13 mg |
| | Microcrystalline cellulose | — mg | — mg | 13 mg |
| | Hydroxypropyl cellulose | 3 mg | 4 mg | 4 mg |
| | Macrogol 6000 | 3 mg | 4 mg | 4 mg |
| Component (B) | Microcrystalline cellulose | — mg | 15 mg | 13 mg |
| | Low substituted Hydroxypropyl cellulose | 9.5 mg | 12.4 mg | 13 mg |
| | Magnesium stearate | 0.5 mg | 0.7 mg | 0.7 mg |
| Film coating | Hypromellose 2910 | 3.007 mg | 3.829 mg | 3.829 mg |
| | Macrogol 6000 | 0.603 mg | 0.768 mg | 0.768 mg |
| | Titanium dioxide | 0.402 mg | 0.512 mg | 0.512 mg |
| | Iron oxide yellow | 0.027 mg | — mg | 0.046 mg |
| | Iron oxide red | 0.009 mg | 0.010 mg | — mg |
| | Macrogol 6000 | 0.060 mg | 0.073 mg | 0.073 mg |
| | Total | 104 mg | 135 mg | 135 mg |
| Shape of score line | Depth of V-shaped groove (d) | 0.54 mm | 0.65 mm | 0.65 mm |
| | Height of elevation of surface of each of upper surface and lower surface (h) | 0.61 mm | 0.687 mm | 0.687 mm |
| | d/h | 0.89 | 0.95 | 0.95 |
| | Inner angle of V shape of V-shaped groove | 70° | 70° | 70° |
| Total thickness of plain tablet (t) | | 3.0 mm | 3.2 mm | 3.2 mm |
| | 2d/t | 0.36 | 0.41 | 0.41 |

TABLE 9

| | | Dosage | | |
|---|---|---|---|---|
| | | 10 mg | 20 mg | 40 mg |
| Uncoated tablet | | | | |
| Component (A) | Hydroxypropyl cellulose | 1590 g | 2120 g | 2120 g |
| | Macrogol 6000 | 1590 g | 2120 g | 2120 g |
| | Purified water | 24910 g | 24380 g | 24380 g |
| | Compound C | 5300 g | 10600 g | 21200 g |
| | Lactose monohydrate | 27030 g | 28570 g | 15530 g |
| | Corn starch | 12190 g | 10600 g | 6890 g |
| | Microcrystalline cellulose | — g | — g | 6890 g |
| Component (B) | Microcrystalline cellulose | — g | 7500 g | 6500 g |
| | Low substituted Hydroxypropyl cellulose | 4750 g | 6200 g | 6500 g |
| | Magnesium stearate | 250 g | 350 g | 350 g |
| Film coating | Hypromellose 2910 | 1353 g | 1723 g | 1723 g |
| | Macrogol 6000 | 271.4 g | 345.6 g | 345.6 g |
| | Titanium dioxide | 180.9 g | 230.4 g | 230.4 g |
| | Iron oxide yellow | 12.15 g | — g | 20.7 g |
| | Iron oxide red | 4.050 g | 4.500 g | — g |
| | Purified water | 16200 g | 13050 g | 13050 g |
| | Macrogol 6000 | 27 g | 32.85 g | 32.85 g |
| | Purified water | 243 g | 295.7 g | 295.7 g |

Comparative Example 1

[Forms and Dimensions of Respective Parts]

The tolerance of the dimension of the punch to be used in the tablet press is from −0.01 mm to −0.05 mm, and the acceptance of the dimension of the die is from +0.01 mm to +0.03 mm.

Peripheral shape of both surfaces of the scored tablet: as shown in FIG. 3(b), an approximately oval shape in which two arc portions with a large radius (radius: 10 mm) are interposed between two arc portions with a small radius (radius: 2.719 mm) and smoothly joined with one another.

Diameter of the major axis L of the oval shape: 12 mm; diameter of the minor axis S: 7 mm; ratio S/L: 0.58

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 1.3 mm Elevation pattern of path of bottom of V-shaped groove: elevation in the form of an arc with a radius of 11.81 mm throughout the entire length.

Depth of V-shaped groove in the center part (dimension d in FIG. 4): 0.4 mm, ratio d/h: 0.31

Dimension in the thickness direction of peripheral side surface (dimension W in FIG. 4): 2 mm Total thickness (dimension t in FIG. 4): 4.6 mm, ratio 2d/t: 0.17

Inner angle of V shape being the shape of cross-section of V-shaped groove: 100°

Production of the Product of Comparative Example

In a fluid bed granulator (FD-WSG-60, Powrex Corporation), according to the formulation shown in Table 3 and the amount of charge shown in Table 4, Compound B, lactose monohydrate and corn starch were uniformly mixed, and the resulting mixture was granulated in the machine by spraying an aqueous solution in which hydroxypropyl cellulose was dissolved and the resulting granules were dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, carmellose calcium and magnesium stearate were added, and all the ingredients were blended in a diffusion mixer (TM-400S, Showa Kagaku Kikai Kosakusho Co., Ltd.), whereby blended granule for compression were prepared.

The resulting blended granules were compressed by a rotary tablet press (Correct 12HUK, Kikusui Seisakusho, Ltd.) using an oval punch with a size of 12.0 mm×7.0 mm (1/L=0.58) having a score line in the form shown in the column "Punch 1" of Table 6 at a compression force level of 9 kN/punch to give a plain tablet having a weight of 300 mg and a thickness of 4.6 mm, whereby the plain tablets were obtained.

In a pan coating equipment (Hicoater HCP-75, Freund Corporation), according to the amount of charge shown in Table 5, a liquid in which hypromellose 2910 and macrogol 6000 were dissolved and titanium dioxide was dispersed was sprayed onto the obtained plain tablets, and further subsequently, a macrogol 6000 solution was sprayed thereonto, whereby film-coated tablet having a score line on both surfaces containing Compound B in an amount of 50 mg per tablet were obtained.

Comparative Example 2

Forms and Dimensions of Respective Parts

The tolerance of the dimension of the punch to be used in the tablet press is from −0.01 mm to −0.05 mm, and the acceptance of the dimension of the die is from +0.01 mm to +0.03 mm.

Peripheral shape of both surfaces of the scored tablet: as shown in FIG. 3(b), an approximately oval shape in which two arc portions with a large radius (radius: 10 mm) are interposed between two arc portions with a small radius (radius: 2.719 mm) and smoothly joined with one another.

Diameter of the major axis L of the oval shape: 12 mm; minor axis S: 7 mm; ratio S/L: 0.58

Elevation pattern of each of upper surface and lower surface: as shown in FIG. 5(c), the elevation pattern is such that the surface is elevated linearly from the peripheral edge at an angle of elevation of 35° and the elevated manner changes to a large radius of curvature.

Height of elevation of each of upper surface and lower surface (dimension h in FIG. 4): 1.3 mm Elevation pattern of path of bottom of V-shaped groove: elevation in the form of an arc with a radius of 11.81 mm throughout the entire length.

Depth of V-shaped groove in the center part (dimension d in FIG. 4): 1.3 mm, ratio d/h: 1

Dimension in the thickness direction of peripheral side surface (dimension W in FIG. 4): 2 mm Total thickness (dimension t in FIG. 4): 4.6 mm, ratio 2d/t: 0.57

Inner angle of V shape being the shape of cross-section of V-shaped groove: 100°

Production of the Product of Comparative Example

In a fluid bed granulator (FD-WSG-60, Powrex Corporation), according to the formulation shown in Table 3 and the amount of charge shown in Table 4, Compound B, lactose monohydrate and corn starch were uniformly mixed, and the resulting mixture was granulated in the machine by spraying an aqueous solution in which hydroxypropyl cellulose was dissolved and the resulting granules were dried therein.

The obtained granules were milled using a screening mill (P-7S, Showa Kagaku Kikai Kosakusho Co., Ltd.) with a punching screen having holes with an inner diameter of 1.5 mm.

To the resulting milled granules, carmellose calcium and magnesium stearate were added, and all the ingredients were blended in a diffusion mixer (TM-400S, Showa Kagaku Kikai Kosakusho Co., Ltd.), whereby blended granules for compression were prepared.

The resulting blended granules were compressed by a rotary tablet press (Correct 12HUK, Kikusui Seisakusho, Ltd.) using an oval punch having a major axis of 12.0 mm and a diameter of a minor axis of 7.0 mm (S/L=0.58) with a score line in the form shown in the column "Punch 4" of Table 6 at a compression force level of 9 kN/punch to give a plain tablet having a weight of 300 mg and a thickness of 4.6 mm, whereby the plain tablets were obtained. In a pan coating equipment (Hicoater HCP-75, Freund Corporation), according to the amount of charge shown in Table 5, a liquid in which hypromellose 2910 and macrogol 6000 were dissolved and titanium dioxide was dispersed was sprayed onto the obtained plain tablet, and further subsequently, a macrogol 6000 solution was sprayed thereonto, whereby film-coated tablets having a score line on both surfaces containing Compound B in an amount of 50 mg per tablet were obtained.

Test Example 1

The film-coated tablets obtained in Example 1 (dose of Compound A (free form): 6.25 mg, 12.5 mg and 25 mg) were evaluated by three panelists (a, b and c) for the content uniformity in the half-divided tablet and the appearance thereof (n=10).

In the content uniformity test, evaluation was carried out using the content uniformity test method and the method for calculating an Acceptance Value according to the 15th revised Japanese Pharmacopoeia (JP) (an Acceptance Value for content uniformity met to the criteria when it is not more than 15%).

The appearance was evaluated using the following marks, which respectively mean the following conditions:

++: An abnormality such as peeling of the film surface is not observed.

+: Although peeling of the film surface is not conspicuous, connection of a film piece to the half tablet on the other side is slightly observed.

−: Peeling of the film surface at the time of dividing is observed.

The results are shown in Table 10.

Figure 11:
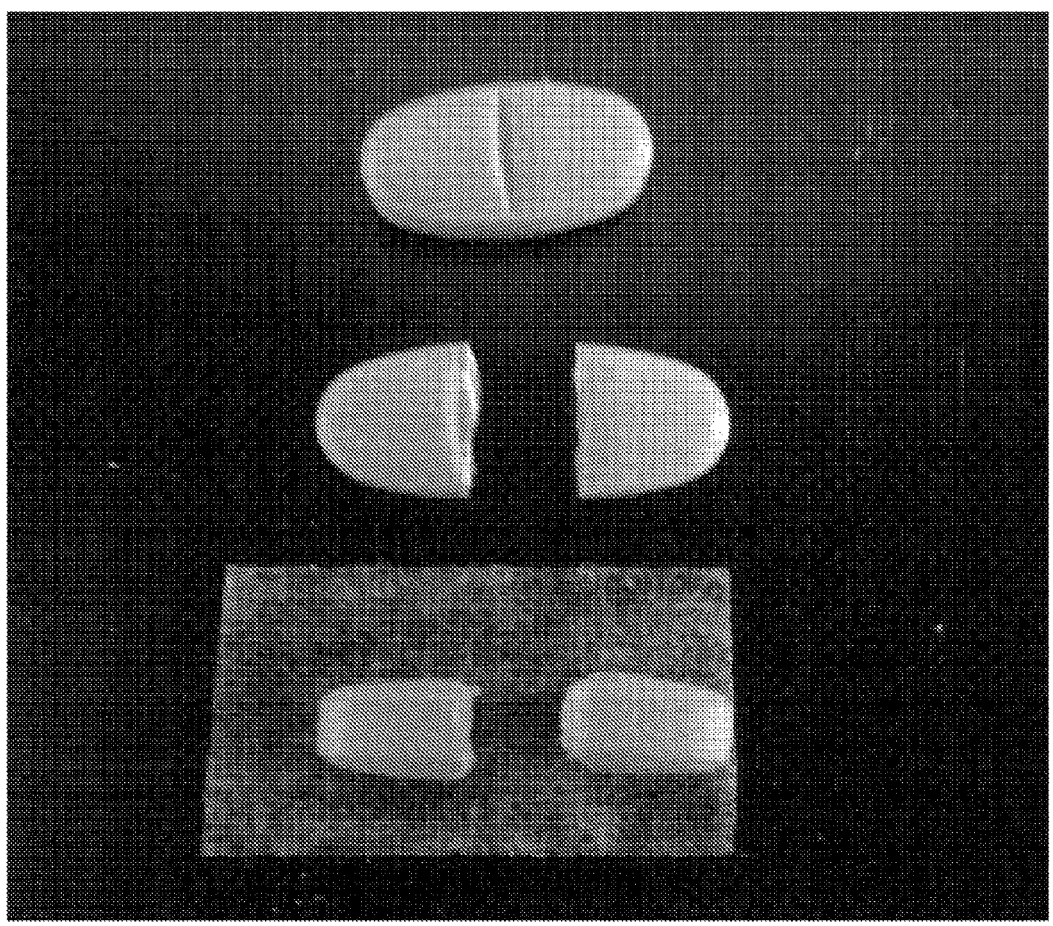
FIG. 11 is a photograph of the tablet of Example 1 (dose of Compound A (free form): 6.25 mg) after the panelist b divided the tablet.
Figure 12:
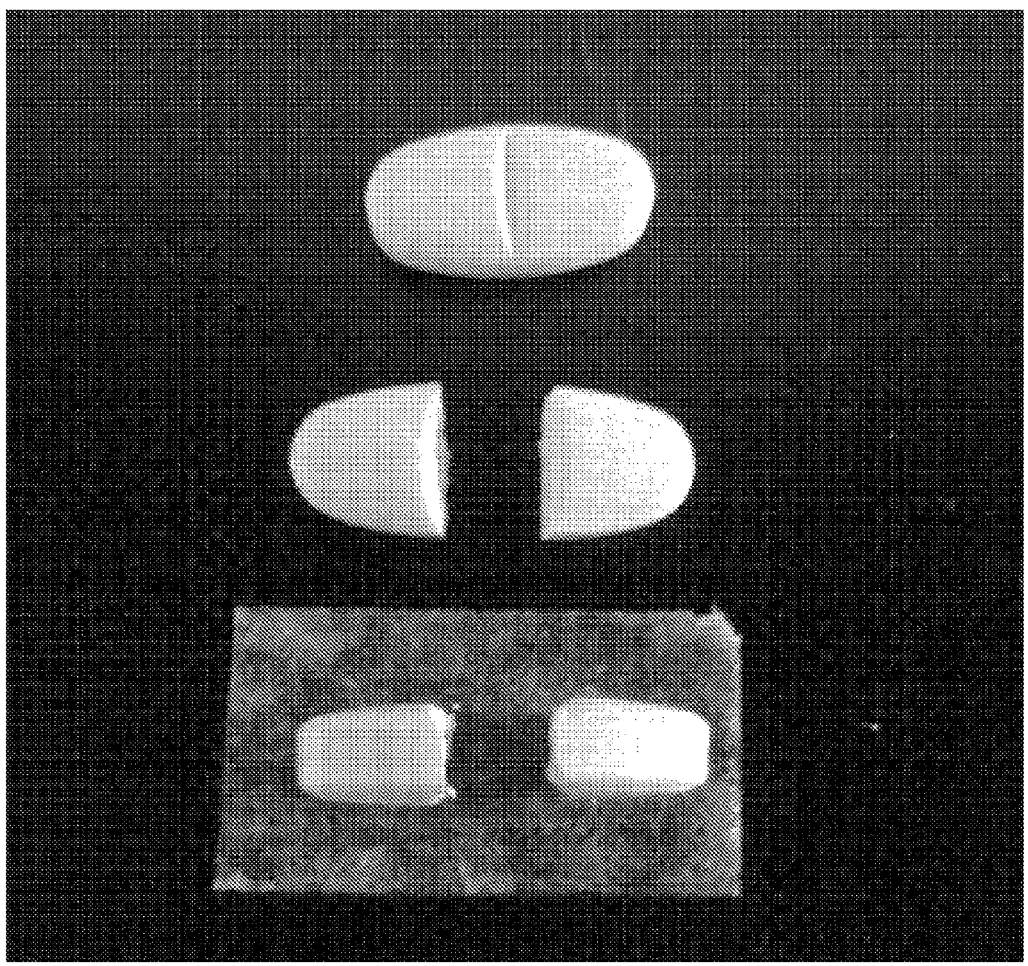
FIG. 12 is a photograph of the tablet of Example 1 (dose of Compound A (free form): 12.5 mg) after the panelist b divided the tablet.
Figure 13:
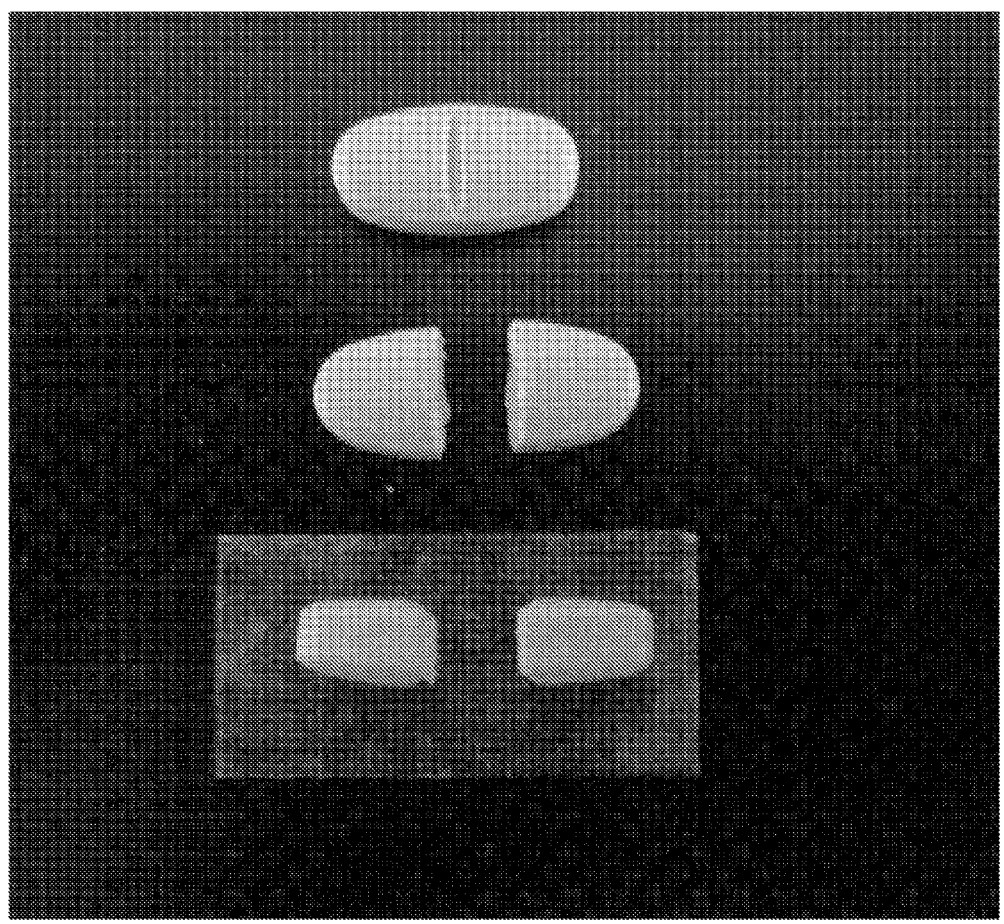
FIG. 13 is a photograph of the tablet of Example 1 (dose of Compound A (free form): 25 mg) after the panelist b divided the tablet.

All of the half tablets after dividing conformed to the determination criteria of a content uniformity test in the Japanese Pharmacopoeia. Further, as for the appearance of the half tablets after dividing, any abnormality such as film peeling was not observed in any tablet (FIGS. 11 to 13).

TABLE 10

| | Dose | Panelist | Content (% relative to labeled amount) Average (n = 10) | Min.-Max. | C.V. (%) | Acceptance Value in the Japanese Pharmacopoeia | Appearance after dividing |
|---|---|---|---|---|---|---|---|
| Example 1 | 6.25 mg | a | 98.6 | 93.3-104.1 | 3.43 | 8.2 | ++ |
| | | b | 99.1 | 95.9-102.2 | 1.89 | 4.6 | ++ (FIG. 11) |
| | | c | 99.1 | 95.3-102.8 | 2.06 | 4.8 | ++ |
| Example 1 | 12.5 mg | a | 99.0 | 95.9-101.5 | 1.81 | 4.3 | ++ |
| | | b | 99.2 | 96.6-102.7 | 2.19 | 5.3 | ++ (FIG. 12) |
| | | c | 99.6 | 97.6-102.0 | 1.50 | 3.6 | ++ |
| Example 1 | 25 mg | a | 99.4 | 96.8-102.3 | 1.82 | 4.3 | ++ |
| | | b | 99.6 | 97.3-101.3 | 1.39 | 3.4 | ++ (FIG. 13) |
| | | c | 100.2 | 98.5-102.4 | 1.21 | 2.9 | ++ |

Test Example 2

The bending strength and hardness (in the major axis direction) of each of the plain tablets (dose of Compound A (free form): 6.25 mg, 12.5 mg and 25 mg) obtained in Reference Example at the respective compression force levels were measured. The respective results are shown in FIG. 14 and FIG. 15.

Figure 14:
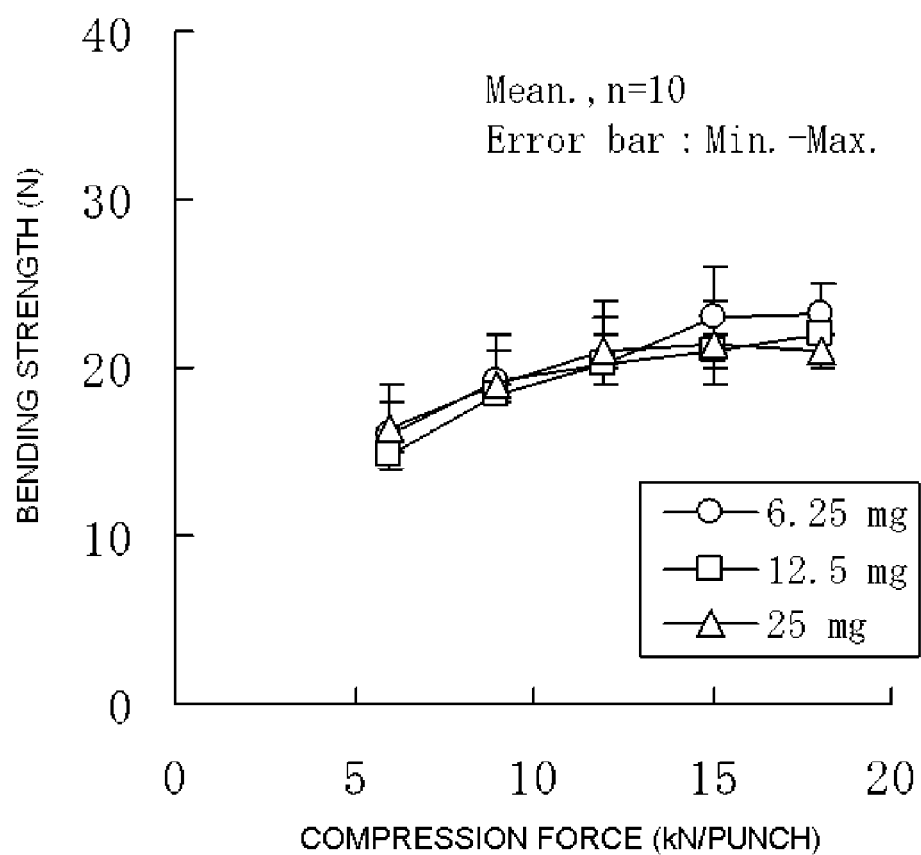
FIG. 14 is a view showing the bending strength (in the major axis direction) of the tablets of Reference Example (dose of Compound A (free form): 6.25 mg, 12.5 mg and 25 mg).
Figure 15:
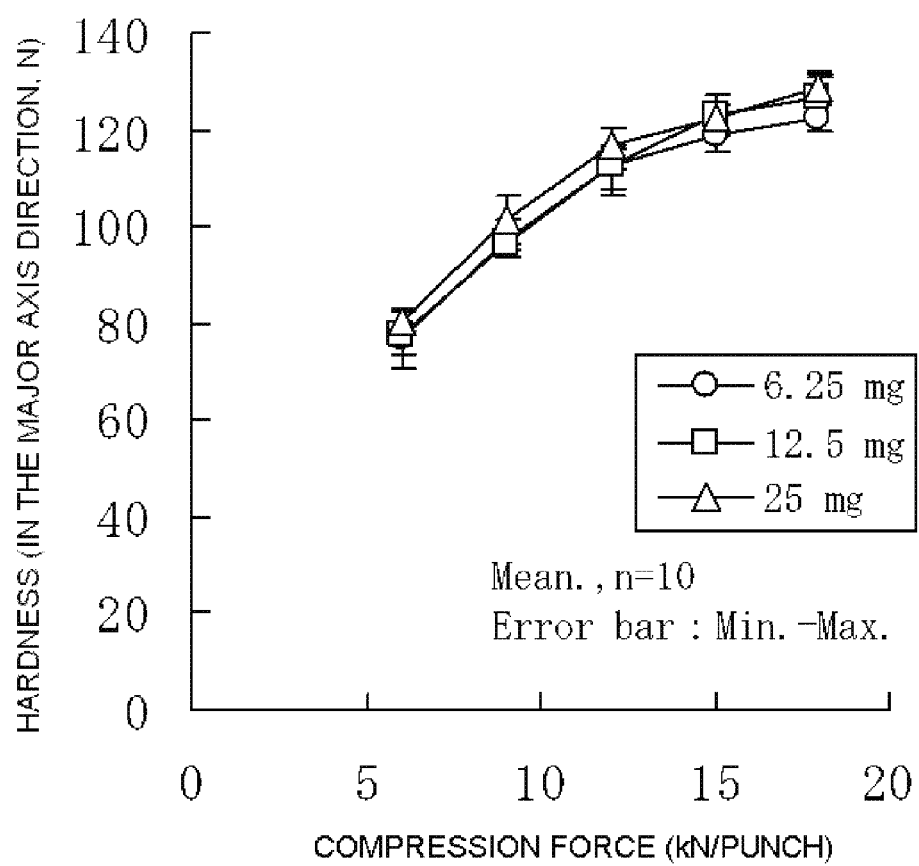
FIG. 15 is a view showing the hardness (in the major axis direction) of the tablets of Reference Example (dose of Compound A (free form): 6.25 mg, 12.5 mg and 25 mg).

As for the profile of the bending strength serving as the index of divisibility, as shown in FIG. 14, the bending strength changed little even if the compression force was increased, and the bending strength was in the range of from 10 N to 40 N at any compression force level. On the other hand, as for the profile of the hardness (in the major axis direction), as shown in FIG. 15, the hardness was improved as the compression force was increased. From these results, it was shown that the tablet formability of the plain tablet is improved by increasing the compression force, but the divisibility thereof is not affected by an increase in the compression force.

Test Example 3

The film-coated tablets obtained in Comparative example 1, Comparative example 2, Example 2 and Example 3 (dose of Compound B: 50 mg) were evaluated for the mass uniformity of the half-divided tablet, bending strength and appearance thereof. Also, a sensory test (ease of dividing) for the divisibility was performed.

The appearance was evaluated using the following marks, which respectively mean the following conditions:

++: An abnormality such as peeling of the film surface is not observed.

+: Although peeling of the film surface is not conspicuous, connection of a film piece to the half tablet on the other side is slightly observed.

−: Peeling of the film surface at the time of dividing is observed.

The sensory evaluation (ease of dividing) was evaluated using the following marks, which respectively mean the following conditions:

A: Dividing is very easy.
B: Dividing is easy.
C: Dividing is somewhat difficult.
D: Dividing is difficult.
E: Dividing is impossible.

The results are shown in Table 11.

Figure 16:
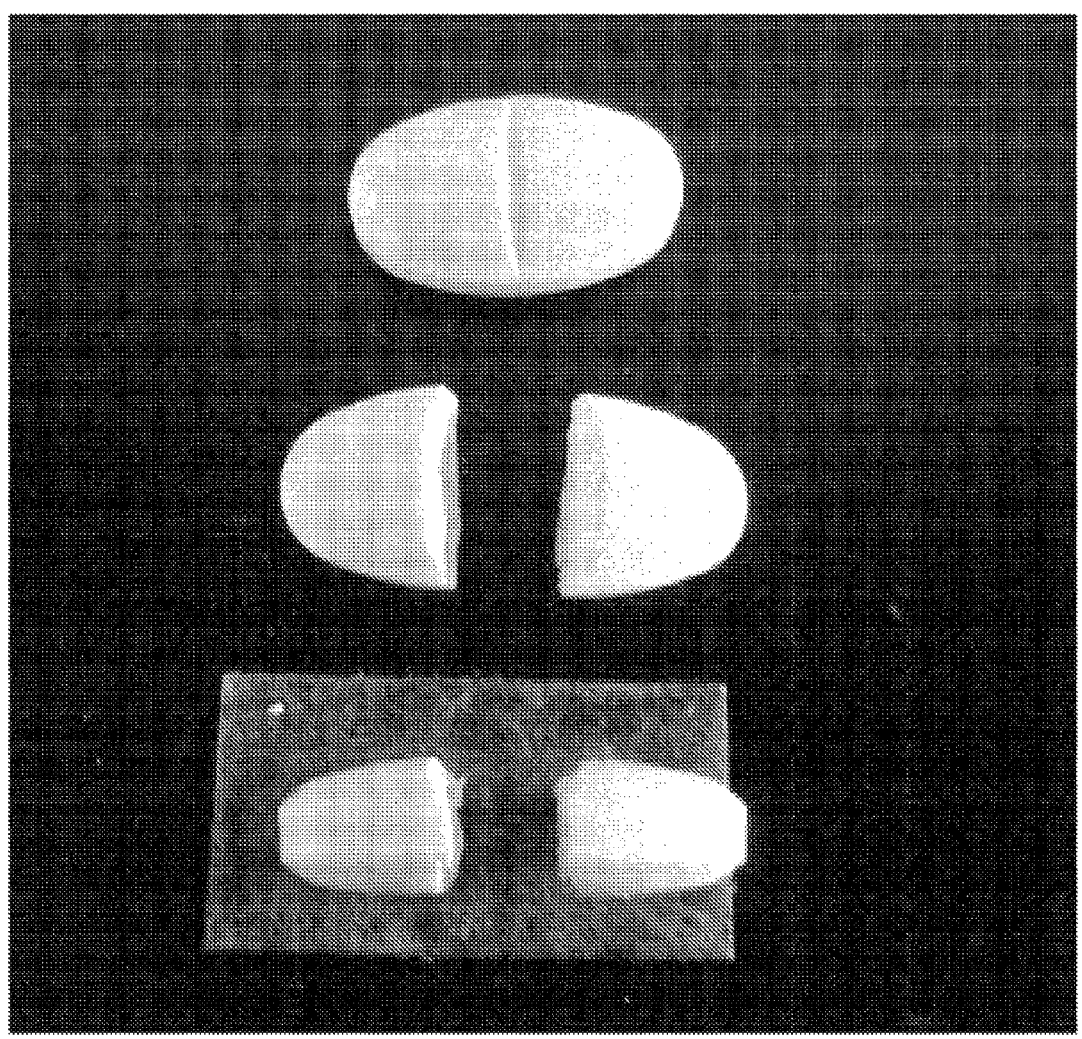
FIG. 16 is a photograph of the tablet of Example 2 (depth of the score line: 0.8 mm) after dividing.
Figure 17:
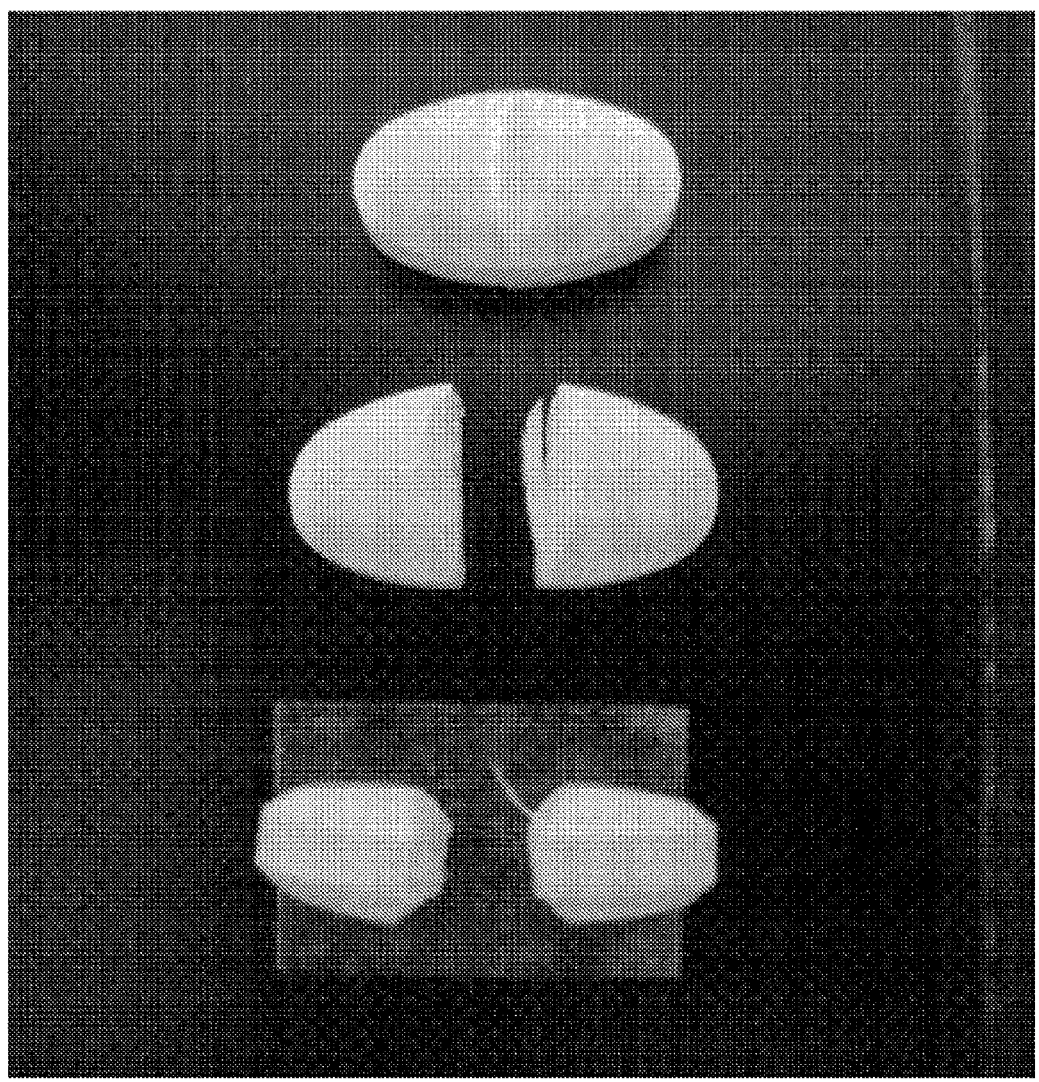
FIG. 17 is a photograph of the tablet of Comparative example 2 (depth of the score line: 1.3 mm) after dividing.

The film-coated tablet (Example 2) in which the depth of the V-shaped groove was 0.8 mm had a favorable divisibility in the sensory evaluation, and also with respect to the appearance of the half tablet after dividing, an abnormality such as film peeling was not observed (FIG. 16). Also, the film-coated tablet (Example 3) in which the depth of the V-shaped groove was 0.6 mm had a favorable divisibility in the sensory evaluation, and also with respect to the appearance of the half tablet after dividing, an abnormality such as film peeling was not observed. On the other hand, although the film-coated tablet (Comparative example 2) in which the depth of the V-shaped groove was 1.3 mm had an extremely favorable divisibility in the sensory evaluation, peeling of the film surface at the time of dividing was observed (FIG. 17). Further, the film-coated tablet (Comparative example 1) in which the depth of the V-shaped groove was 0.4 mm was somewhat difficult to divide in the sensory evaluation, and although peeling of the film surface at the time of dividing was not conspicuous, connection of a film piece to the half tablet on the other side after dividing was slightly observed.

TABLE 11

|  | Depth of V-shaped groove (d) | Weight of half tablet (mg) Average (n = 10) | C.V. (%) | Bending strength (N) | Appearance after dividing | Sensory evaluation (ease of dividing) |
|---|---|---|---|---|---|---|
| Comparative example 1 | 0.4 mm | 155.5 | 3.00 | 43.8 | + | C |
| Example 3 | 0.6 mm | 155.4 | 1.58 | 41.9 | ++ | B |
| Example 2 | 0.8 mm | 155.8 | 2.51 | 25.2 | ++ | A |
| Comparative example 2 | 1.3 mm | 155.8 | 1.34 | 17.4 | — | A |

Test Example 4

With respect to the film-coated tablets obtained in Example 4 (dosages of Compound C: 10 mg, 20 mg and 40 mg), the content uniformity and appearance of the half-divided tablets divided by 3 panelists (a, b and c) were evaluated (n=10). The results are shown in Table 12. In this regard, the content of a half-divided tablet was calculated as a content estimate based on the mass of the half-divided tablet, regarding the average mass of the content of the half-divided tablet as 100%.

All the half-divided tablets were judged as appropriate in the aforementioned content uniformity test of JP. Further, the appearance of the half-divided tablets was evaluated using the following marks, which respectively mean the following conditions:

++: An abnormality such as peeling of the film surface is not observed.

+: Although peeling of the film surface is not conspicuous, connection of a film piece to the half tablet on the other side is slightly observed.

−: Peeling of a film surface at the time of dividing was found.

Figure 18:
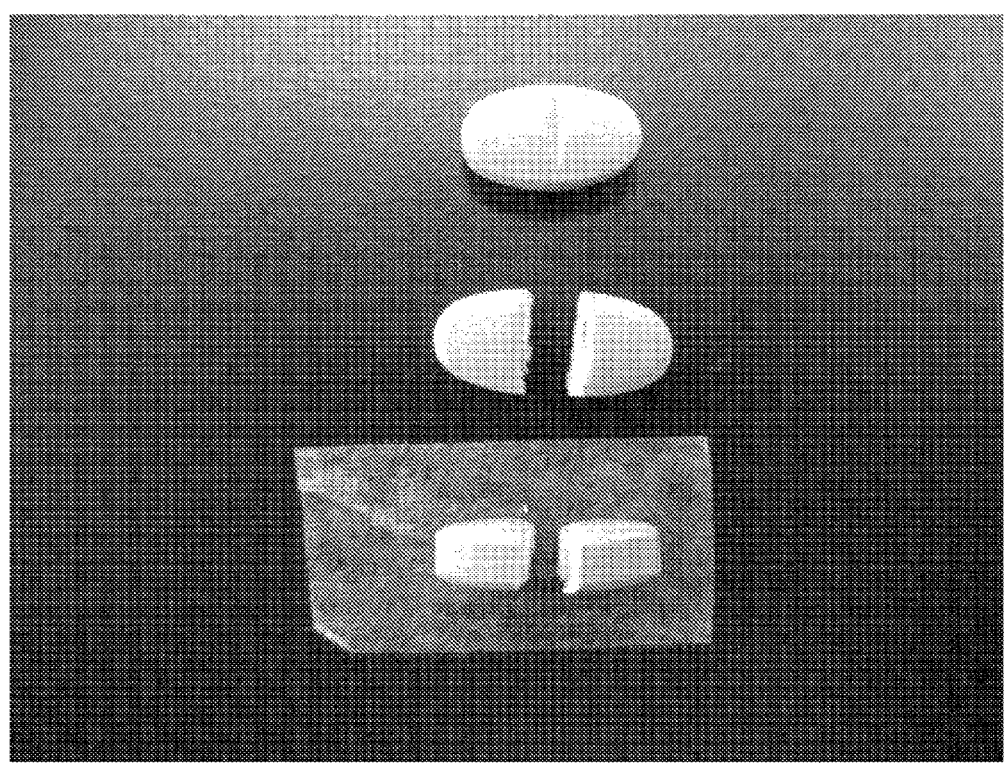
FIG. 18 is a photograph of a tablet of Example 4 (dosage of Compound C: 10 mg) after the panelist b divided the tablet.
Figure 19:
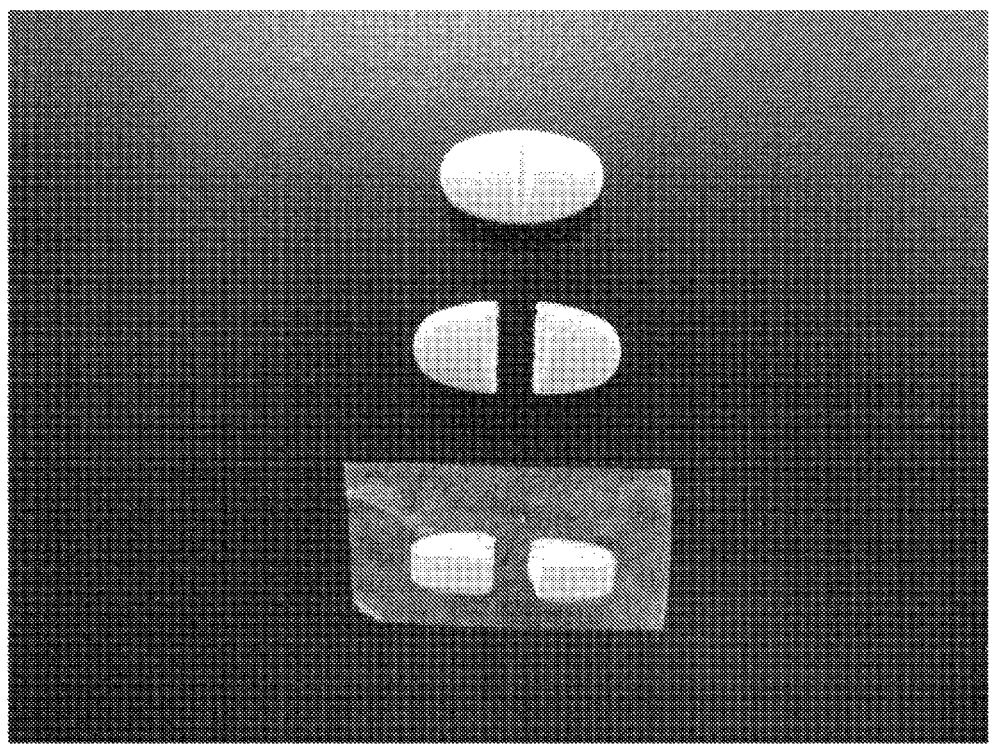
FIG. 19 is a photograph of a tablet in Example 4 (dosage of Compound C: 20 mg) after the panelist b divided the tablet.
Figure 20:
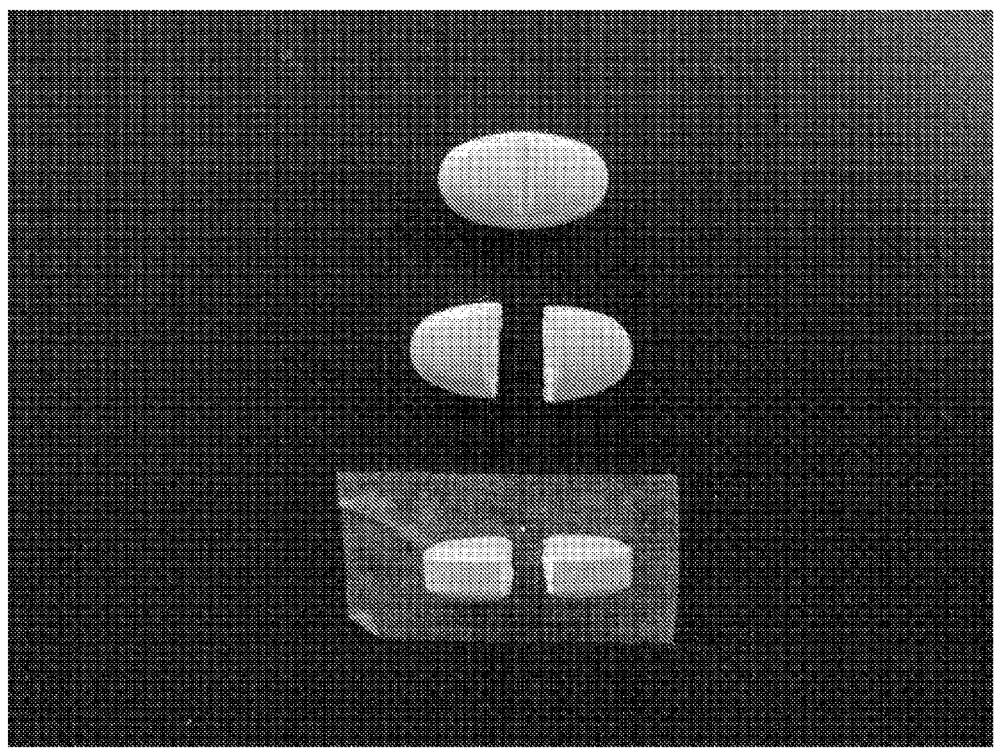
FIG. 20 is a photograph of a tablet in Example 4 (dosage of Compound C: 40 mg) after the panelist b divided the tablet.

Regarding all the half-divided tablets, no abnormity (e.g., peeling of a film) was found (FIGS. 18-20).

TABLE 12

| | | Mass variation test | | | | | | |
|---|---|---|---|---|---|---|---|---|
| | | Left side (n = 10) | | | Right side (n = 10) | | | |
| Dosage | Panelist | Min.-Max. | C.V. (%) | Acceptance value | Min.-Max. | C.V. (%) | Acceptance value | Appearance after divided |
| 10 mg | a | 95.7-103.0 | 2.8 | 6.6 | 95.8-107.1 | 3.5 | 8.5 | ++ |
| | b | 95.1-107.7 | 4.7 | 11.5 | 91.2-105.4 | 5.3 | 12.5 | ++ (FIG. 18) |
| | c | 93.0-102.9 | 2.9 | 6.9 | 96.7-104.9 | 2.4 | 6.0 | ++ |

TABLE 12-continued

| | | Mass variation test | | | | | | |
|---|---|---|---|---|---|---|---|---|
| | | Left side (n = 10) | | | Right side (n = 10) | | | |
| Dosage | Panelist | Min.-Max. | C.V. (%) | Acceptance value | Min.-Max. | C.V. (%) | Acceptance value | Appearance after divided |
| 20 mg | a | 95.4-105.3 | 3.0 | 7.2 | 94.5-105.9 | 3.0 | 7.1 | ++ |
| | b | 93.6-100.6 | 2.5 | 7.0 | 99.1-106.5 | 2.5 | 7.2 | ++ (FIG. 19) |
| | c | 97.7-101.8 | 1.4 | 3.5 | 97.4-103.1 | 1.6 | 3.9 | ++ |
| 40 mg | a | 98.9-101.4 | 0.8 | 1.8 | 98.0-100.8 | 1.0 | 2.3 | ++ |
| | b | 95.3-101.3 | 1.8 | 4.3 | 97.5-104.2 | 2.0 | 4.8 | ++ (FIG. 20) |
| | c | 96.9-104.7 | 2.4 | 5.7 | 96.0-102.4 | 2.1 | 5.0 | ++ |

From the above results, it was shown that according to the invention, a film-coated tablet showing a favorable divisibility without causing film peeling at the time of dividing can be obtained.

INDUSTRIAL APPLICABILITY

According to the invention, when a film-coated scored tablet is divided, the film is more preferably divided along the score line.

| Description of Reference Numerals and Signs | |
|---|---|
| 1 | Upper surface |
| 2 | Lower surface |
| 3 | Peripheral side surface |
| 4 | V-shaped groove (score line) |
| 41 | Bottom of V-shaped groove |
| L | Diameter of major axis of oval shape |
| S | Diameter of minor axis of oval shape |
| d | Depth of V-shaped groove |
| h | Height of elevation of upper surface or lower surface |
| t | Total thickness |
| θ | Inner angle of V shape of V-shaped groove |

The invention claimed is:

1. A film-coated scored tablet comprising a tablet being coated with a film coating on a plain tablet having score lines, wherein
the scored tablet has an upper surface and a lower surface whose peripheral shape is an oval shape, and a peripheral side surface, the upper surface and the lower surface are gradually elevated from the peripheral edge toward the center thereof, and a V-shaped groove as the score line is provided on each of the upper surface and the lower surface along the minor axis of the oval shape;
an inner angle of the V shape of the V-shaped groove is from 50° to 90°;
a path of the bottom of the V-shaped groove is elevated more on the center side than on the peripheral edge sides of each of the upper surface and the lower surface;
a ratio of a depth d of the V-shaped groove in the center of each of the upper surface and the lower surface to a height h of the elevation of the surface (d/h) is from 0.4 to 0.9; and
a ratio of a value obtained by doubling the depth d of the V-shaped groove (2d) in the center of each of the upper surface and the lower surface to a total thickness t of the scored tablet (2d/t) is from 0.2 to 0.4.

2. The film-coated scored tablet according to claim 1, wherein the oval shape is an oval shape which does not have straight-line portions.

3. The film-coated scored tablet according to claim 1, wherein a ratio of the diameter of the minor axis S to the diameter of the major axis L (S/L) of the oval shape is from 0.4 to 0.6.

4. The film-coated scored tablet according to claim 1, wherein the diameter of the major axis L of the oval shape is from 8 mm to 12 mm.

5. The film-coated scored tablet according to claim 1, wherein the inner angle of the V shape of the V-shaped groove is 70°.

6. The film-coated scored tablet according to claim 1, wherein the depth d is from 0.5 to 0.8 mm.

7. The film-coated scored tablet according to claim 1, wherein a bending strength represented by a force required for dividing the film-coated scored tablet when the force is applied thereto so as to divide the tablet at the score line is 50 N or less.

8. The film-coated scored tablet according to claim 1, which contains 2-({6-[(3R)-3-aminopiperidin-1-yl]-3-methyl-2,4-dioxo-3,4-dihydropyrimidin-1(2H)-yl}methyl)benzonitrile or a salt thereof.

9. The film-coated scored tablet according to claim 1, which contains 2-ethoxy-1-[[2'-(5-oxo-2,5-dihydro-1,2,4-oxadiazol-3-yl)biphenyl-4-yl]methyl]-1H-benzimidazole-7-carboxylic acid or a salt thereof.

* * * * *